(12) United States Patent
Yan et al.

(10) Patent No.: US 10,709,708 B2
(45) Date of Patent: Jul. 14, 2020

(54) METHOD OF TREATING CANCER WITH A COMBINATION OF MER TYROSINE KINASE INHIBITOR AND AN EPIDERMAL GROWTH FACTOR RECEPTOR (EGFR) INHIBITOR

(71) Applicants: Emory University, Atlanta, GA (US); The University of North Carolina at Chapel Hill, Chapel Hill, NC (US)

(72) Inventors: Dan Yan, Lilburn, GA (US); H. Shelton Earp, III, Chapel Hill, NC (US); Deborah Ann DeRyckere, Atlanta, GA (US); Douglas Kim Graham, Atlanta, GA (US); Jing Wan, Chapel Hill, NC (US)

(73) Assignees: The University of North Carolina at Chapel Hill, Chapel Hill, NC (US); Emory University, Atlanta, GA (US)

( * ) Notice: Subject to any disclaimer, the term of this patent is extended or adjusted under 35 U.S.C. 154(b) by 316 days.

(21) Appl. No.: 15/462,299

(22) Filed: Mar. 17, 2017

(65) Prior Publication Data
US 2017/0266188 A1    Sep. 21, 2017

Related U.S. Application Data

(60) Provisional application No. 62/309,772, filed on Mar. 17, 2016.

(51) Int. Cl.
*A61K 31/519*    (2006.01)
*A61K 31/5377*    (2006.01)
*A61K 45/06*    (2006.01)

(52) U.S. Cl.
CPC ........ *A61K 31/519* (2013.01); *A61K 31/5377* (2013.01); *A61K 45/06* (2013.01)

(58) Field of Classification Search
CPC ................ A61K 31/506; A61K 31/519; A61K 31/5377; A61K 45/06
See application file for complete search history.

(56) References Cited

U.S. PATENT DOCUMENTS

| | | | |
|---|---|---|---|
| 5,958,930 A | 9/1999 | Gangjee et al. |
| 7,217,710 B2 | 5/2007 | Adams et al. |
| 7,589,086 B2 | 9/2009 | Bondavelli et al. |
| 7,897,607 B2 | 3/2011 | Gyorkos et al. |
| 7,956,060 B2 | 6/2011 | Arai et al. |
| 7,998,978 B2 | 8/2011 | Huang et al. |
| 8,324,225 B2 | 12/2012 | Brain et al. |

(Continued)

FOREIGN PATENT DOCUMENTS

| | | |
|---|---|---|
| CA | 2492319 | 4/2004 |
| EP | 1710246 A1 | 10/2006 |

(Continued)

OTHER PUBLICATIONS

Anderson (Chem and Biol 10:787-797, 2003), (Year: 2003).*

(Continued)

*Primary Examiner* — Savitha M Rao
(74) *Attorney, Agent, or Firm* — Alston & Bird, LLP

(57) ABSTRACT

The invention provides combinations comprising a MERTK inhibitor, or a pharmaceutically acceptable salt thereof, and an EGFR inhibitor and methods of use thereof, including methods of treating disorders such as cancer.

9 Claims, 18 Drawing Sheets

(56) References Cited

U.S. PATENT DOCUMENTS

| | | | |
|---|---|---|---|
| 8,362,023 B2 | 1/2013 | Liu et al. | |
| 8,415,361 B2 | 4/2013 | Lemke et al. | |
| 8,513,242 B2 | 8/2013 | Chiang et al. | |
| 9,273,056 B2 | 3/2016 | Wang et al. | |
| 9,290,499 B2 | 3/2016 | Wang et al. | |
| 9,555,030 B2 | 1/2017 | Wang et al. | |
| 9,555,031 B2 | 1/2017 | Wang et al. | |
| 9,562,047 B2 | 2/2017 | Wang et al. | |
| 9,567,326 B2 | 2/2017 | Wang et al. | |
| 9,603,850 B2 | 3/2017 | Wang et al. | |
| 9,649,309 B2 | 5/2017 | Wang et al. | |
| 2004/0209895 A1 | 10/2004 | Luecking et al. | |
| 2005/0101617 A1* | 5/2005 | Wallace | C07D 239/94 514/266.2 |
| 2006/0025383 A1 | 2/2006 | Wishart et al. | |
| 2007/0078140 A1 | 4/2007 | Borzilleri et al. | |
| 2007/0105874 A1 | 5/2007 | Zhang et al. | |
| 2007/0225306 A1 | 9/2007 | Choi et al. | |
| 2007/0275984 A1 | 11/2007 | Imogai et al. | |
| 2008/0125448 A1* | 5/2008 | Qian | C07D 239/94 514/266.4 |
| 2008/0248046 A1 | 10/2008 | Ni et al. | |
| 2008/0267887 A1 | 10/2008 | Yuan et al. | |
| 2009/0012061 A1 | 1/2009 | Arai et al. | |
| 2010/0137313 A1 | 6/2010 | Bonack-Sjodin et al. | |
| 2010/0247554 A1 | 9/2010 | Lemke et al. | |
| 2010/0266604 A1 | 10/2010 | Rothlin et al. | |
| 2011/0281867 A1 | 11/2011 | Kalman et al. | |
| 2011/0319267 A1 | 12/2011 | Ekwuribe et al. | |
| 2012/0035194 A1 | 2/2012 | Huang et al. | |
| 2012/0207763 A1 | 8/2012 | Brain et al. | |
| 2012/0207764 A1 | 8/2012 | Terrett et al. | |
| 2012/0219559 A1 | 8/2012 | Chen et al. | |
| 2012/0230991 A1 | 9/2012 | Graham et al. | |
| 2013/0029993 A1 | 1/2013 | Stadtmueller | |
| 2013/0034862 A1 | 2/2013 | Fantl et al. | |
| 2013/0059836 A1 | 3/2013 | Wang et al. | |
| 2013/0072382 A1 | 3/2013 | Trullinger et al. | |
| 2013/0102587 A1 | 4/2013 | Evans et al. | |
| 2013/0137708 A1 | 5/2013 | Garske et al. | |
| 2013/0150368 A1 | 6/2013 | Ashcraft et al. | |
| 2013/0266563 A1 | 10/2013 | Gokaraju et al. | |
| 2015/0290194 A1 | 10/2015 | Wang et al. | |
| 2015/0290197 A1* | 10/2015 | Wang | A61K 31/55 424/184.1 |
| 2015/0291606 A1 | 10/2015 | Wang et al. | |
| 2015/0291609 A1 | 10/2015 | Wang et al. | |
| 2015/0322019 A1 | 11/2015 | Wang et al. | |

FOREIGN PATENT DOCUMENTS

| | | |
|---|---|---|
| EP | 2133095 A1 | 3/2007 |
| EP | 1803723 A1 | 7/2007 |
| EP | 2840080 A1 | 12/2009 |
| EP | 2489663 A1 | 8/2012 |
| WO | WO 1997/049706 A1 | 12/1997 |
| WO | WO 2003/029209 A2 | 4/2003 |
| WO | WO 2005/009443 A1 | 2/2005 |
| WO | WO 2005/028434 A2 | 3/2005 |
| WO | WO 2005/095382 A1 | 10/2005 |
| WO | WO 2006/035067 A2 | 4/2006 |
| WO | WO 2006/071819 A1 | 7/2006 |
| WO | WO 2007/032445 A1 | 3/2007 |
| WO | WO 2007/035963 A2 | 3/2007 |
| WO | WO 2007/041379 A1 | 4/2007 |
| WO | WO 2007/044426 A2 | 4/2007 |
| WO | WO 2007/075554 A2 | 7/2007 |
| WO | WO 2007/113254 A1 | 10/2007 |
| WO | WO 2007/134828 A1 | 11/2007 |
| WO | WO 2009/032694 A1 | 3/2009 |
| WO | WO 2009/047359 A1 | 4/2009 |
| WO | WO 2010/043865 A1 | 4/2010 |
| WO | WO 2010/085597 A1 | 7/2010 |
| WO | WO 2010/117425 A1 | 10/2010 |
| WO | WO 2010/129802 A1 | 11/2010 |
| WO | WO 2011/029915 A1 | 3/2011 |
| WO | WO 2011/065800 A2 | 6/2011 |
| WO | WO 2011/090760 A1 | 7/2011 |
| WO | WO 2011/103441 A1 | 8/2011 |
| WO | WO 2011/146313 A1 | 11/2011 |
| WO | WO 2012/053606 A1 | 4/2012 |
| WO | WO 2012/158795 A1 | 11/2012 |
| WO | WO 2013/032591 A1 | 3/2013 |
| WO | WO 2013/042006 A1 | 3/2013 |
| WO | WO 2013/052417 A1 | 4/2013 |
| WO | WO 2013/124324 A1 | 8/2013 |
| WO | WO 2013/157022 A1 | 10/2013 |
| WO | WO 2013/177168 A1 | 11/2013 |
| WO | WO 2014/062774 A1 | 4/2014 |
| WO | WO 2014/085225 A1 | 6/2014 |
| WO | WO 2015/153978 | 10/2015 |
| WO | WO 2015/157115 | 10/2015 |
| WO | WO 2015/157122 | 10/2015 |
| WO | WO 2015/157127 | 10/2015 |
| WO | WO 2015/157128 | 10/2015 |

OTHER PUBLICATIONS

Thiel (Nature Biotechnol 2:513-519, 2004), (Year: 2004).*

Aly et al. "Heteroannelations with o-amino aldehyde and o-amino of some pyrazole derivatives" *Afinidad*, Barcelona, ES (2004) 61:510-515.

Angelillo-Scherrer et al. "Role of Gas6 receptors in platelet signaling during thrombus stabilization and implications for antithrombotic therapy", *J. Clin. Invest.* (2005) 115(2):237-246.

Banker et al. Modern Pharmaceuticals p. 596 (1996).

Bernsmeier, et al. "Patients with Acute-on-Chronic Liver Failure Have Increased Numbers of Regulatory Immune Cells Expressing the Receptor Tyrosine Kinase MERTK", *Gastroenterology* (2015), 1-13.

Bhattacharayya, et al. "Enveloped viruses disable innate immune responses in dendritic cells by direct activation of TAM receptors", *Cell Host & Microbe* (2013) 14:136-147.

Brindley, et al. "Tyrosine kinase receptor Axl enhances entry of Zaire ebolavirus without direct interactions with the viral glycoprotein", *Virology* (2011) 415:83-84.

Cancer Drug Design and Discovery, Neldie, Stephen, ed. (Elsevier/Academic Press, 2008) pp. 427431.

Cavasotto et al. "In silico identification of novel EGFR inhibitors with antiproliferative activity against cancer cells" *Bioorg. Med. Chem. Lett.* (2006) 16:1969-1974.

Chen, et al, "Mer Receptor tyrosine Kinase Signaling Participates in Platelet Function", *Arterioscler. Thromv Vasc. Biol.* (2004) 24:1118-1123.

Chen, et al. "Identification of Gas6 as a ligand for Mer, a neural cell adhesion molecule related receptor tyrosine kinase implicated in cellular transformation", *Oncogene* (1997) 14:2033-2039.

Christoph, S. et al. "UNC569, a novel small-molecule Mer inhibitor with efficacy against acute lymphoblastic leukemia in vitro and in vivo", *Mol Cancer Ther.* (2013) 12(11):2367-77.

Cook, et al. "MerTK inhibition in tumor leukocytes decreases tumor growth and metastasis" *J. Clin. Invest.* (2013) 123:3231-3242.

Database CAPLUS [Online]—Chemical Abstracts Service, Columbus, Ohio, US; 2004, Ismail, M.A.: "Efficient synthesis of 5-(5-aryl-2-furyl)pyrimidine derivatives", Database accession No. 2004:551368: & Ismail., M.A.: "Efficient synthesis of 5-(5-aryl-2-furyl)pyrimidine derivatives", Mansoura Science Bulletin, A: Chemistry, vol. 30, No. 2, 2003, pp. 157-172 (Abstract Only).

Database CAPLUS in STN, Ace. No. 2007:1144983, Guillemont et al., WO 2007/113254 A1 (Oct. 11, 2007)(abstract).

Earp, S. "Chemical Biology Consortium: Mer Kinase Inhibitor Studies" Presentation at the Chemical Biology Consortium, Jan. 26, 2012.

European Search Report for European Application No. 13793925.2 dated Nov. 30, 2015.

European Search Report for European Application No. 13858989.6 dated May 3, 2016.

(56) References Cited

OTHER PUBLICATIONS

European Search Report for European Application No. 13847985.2 dated May 24, 2016.
Extended European Search Report, EP 11783985.2, dated Oct. 15, 2013.
Extended European Search Report, EP 12839069.7, dated May 4, 2015.
Frye, S. "Academic Drug Discovery and Chemical Biology", Presentation at the Northwestern 18th Annual Drug Discovery Symposium. Nov. 13, 2013.
Frye, S. "Academic Drug Discovery: US Perspective and Examples" Presentation at the NCI Translational Science Meeting, Washington DC, Jul. 29, 2011.
Graham, et al. "Cloning and mRNA expression analysis of a novel human protooncogene, c-mer", *Cell Growth Differ.* (1994) 5:647-657.
International Premilinary Report on Patentability for International Application No. PCT/US2011/036215, dated Nov. 29, 2012.
International Preliminary Report on Patentability for International Application No. PCT/US2013/042033, dated Dec. 4, 2014.
International Preliminary Report on Patentability for International Application No. PCT/US2013/065192, dated Apr. 30, 2015.
International Preliminary Report on Patentability for International Application No. PCT/US2013/071409, dated Jun. 11, 2015.
International Search Report and Written Opinion for International Application No. PCT/US2011/036215, dated Aug. 16, 2011.
International Search Report and Written Opinion for International Application No. PCT/US2012/058298, dated Dec. 7, 2012.
International Search Report and Written Opinion for International Application No. PCT/US2013/042033, dated Aug. 27, 2013.
International Search Report and Written Opinion for International Application No. PCT/US2013/065192, dated Jan. 24, 2014.
International Search Report and Written Opinion for International Application No. PCT/US2013/071409, dated Mar. 31, 2014.
International Search Report and Written Opinion, PCT/US2015/24258, dated Jun. 24, 2015.
International Search Report and Written Opinion, PCT/US2015/243301, dated Jun. 25, 2015.
International Search Report and Written Opinion, PCT/US2015/24328, dated Jun. 25, 2015.
International Search Report and Written Opinion, PCT/US2015/24362, dated Jun. 26, 2015.
International Search Report and Written Opinion, PCT/US2015/24373, dated Jul. 7, 2015.
International Search Report and Written Opinion, PCT/US2015/24380, dated Jul. 1, 2015.
International Search Report and Written Opinion, PCT/US2015/24381, dated Jul. 1, 2015.
Kiyoi et al, "A Novel FLT3 Inhibitor F1-700 Selectively Suppresses the Growth of Leukemia Cells with FLT3 Mutations", Clin Cancer Res 13(15):4575-4582 (2007).
Lee-Sherick, et al. "Efficacy of a Mer and Flt3 tyrosine kinase small molecule inhibitor, UNC1666, in acute myeloid leukemia", *Oncotarget*, Advance Publications, Feb. 10, 2015.
Linger et al. "Mer receptor tyrosine kinase is a therapeutic target in pre-B-cell acute lymphoblastic leukemia" *Blood* (2013) 122(9):1599-1609.
Liu, J, et al. "UNC1062, a new and potent Mer inhibitor", *Eur J Med Chem.* (2013) 65:83-93.
Liu, J. et al. "Discovery of Small Molecule Mer Kinase Inhibitors for the Treatment of Pediatric Acute Lymphoblastic Leukemia" *ACS Med. Chem. Left.* (2012) 3(2):129-134.

Ishida et al. "Novel and orally active 5-(1,3,4-oxadiazol-2-Apyrimidine derivatives as selective FLT3 inhibitors", Bioomanic & Medicinal Chemistry Letters 18:5472-5477.
Meertens, L. et al. "The TIM and TAM families of phosphatidylserine receptors mediate dengue virus entry", *Cell Host Microbe* (2012) 12:544-557.
Mercer, J. & Helenius, A. "Vaccinia virus uses macropinocytosis and apoptotic mimicry to enter host cells", *Science* (2008) 320: 531-535.
Morizono and Chen, "Role of Phosphatidyl Receptors in Enveloped Virus Infection", *J. Virology* (2014) 88(8):4275-4290.
Morizono, et al, "The Soluble Serum Protein Gas6 Bridges Virion Envelope Phosphatidylserine to the TAM Receptor Tyrosine Kinase Axl to mediate Viral Entry", *Cell Host & Microbe* (2011) 9:286-298.
Notification Concerning Transmittal of International Preliminary Report on Patentability corresponding to International Application No. PCT/US2015/024381 dated Oct. 20, 2016.
Notification Concerning Transmittal of International Preliminary Report on Patentability corresponding to International Application No. PCT/US2015/024362 dated Oct. 20, 2016.
Notification Concerning Transmittal of International Preliminary Report on Patentability corresponding to International Application No. PCT/US2015/024328 dated Oct. 20, 2016.
Notification Concerning Transmittal of International Preliminary Report on Patentability corresponding to International Application No. PCT/US2015/024258 dated Oct. 13, 2016.
Notification Concerning Transmittal of International Preliminary Report on Patentability corresponding to International Application No. PCT/US2015/024373 dated Oct. 20, 2016.
Notification Concerning Transmittal of International Preliminary Report on Patentability corresponding to International Application No. PCT/US2015/024380 dated Oct. 20, 2016.
Paolino, M., et al. "The E3 ligase Cbl-b and TAM receptors regulate cancer metastasis via natural killer cells", *Nature* (2014) 507:508-512.
Pawar et al. Synthesis of 2,4,5-Trisubstituted Pyrimidinee, Indian Journal of Heterocyclic Chemistry 20(12):133-136 (2010).
Powell et al. "Highly selective 2,4-diaminopyridine-5-carboxamide inhibitors of Sky kinase", *Bioorg. Med. Chem. Lett.* (2013) 23:1046-1050.
Powell et al. "Optimization of highly selective 2,4-diaminopyridine-5-carboxamide inhibitors of Sky kinase", *Bioorg. Med. Chem. Lett.* (2013) 23:1051-1055.
Sather, et al. "A soluble form of the Mer receptor tyrosine kinase inhibits macrophage clearance of apoptotic cells and platelet aggregation", *Blood* (2007) 109(3):1026-1033.
Schlegel et al. "MER receptor tyrosine kinase is a therapeutic target in melanoma" *J. Clin. Invest.* (2013) 123(5): 2257-67.
Shimojima, et al. "Tyro3 Family-mediated Cell Entry of Ebola and Marburg Viruses", *Journal of Virology* (2006) 80(20):10109-10116.
Verma et al."Targeting Axl and Mer Kinases in Cancer", Mel Cancer Thor 10(10)1763-73 (2011).
Wolff et al. "Burger's Medicinal Chemistry and Drug Discovery", John Wiley & Sons, Inc. $5^{th}$ Ed. vol. 1:975-977 (1995).
Yu et al. "30-QSAR modeling and molecular docking study on Mer kinase inhibitors of pyridine. substituted pyrimidines", Mol Divers 19:135-147 (2015).
Zhang et al. "Pseudo-Cyclization through Intramolecular Hydrogen Bond Enables Discovery of Pyridine Substituted Pyrimidines as New Mer Kinase", J. Med. Chem. 56:9683-9692 (2013).
Zhang, W., et al. "Discovery of Mer specific tyrosine kinase inhibitors for the treatment and prevention of thrombosis", *J. Med. Chem.* (2013) 56:9693-9700.

* cited by examiner

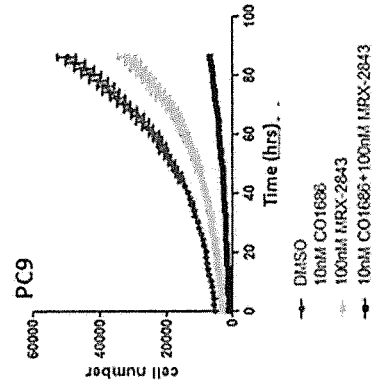
FIG. 9A
FIG. 9B
FIG. 9C
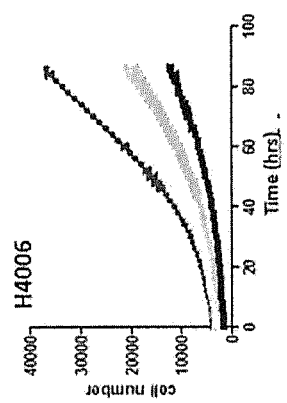
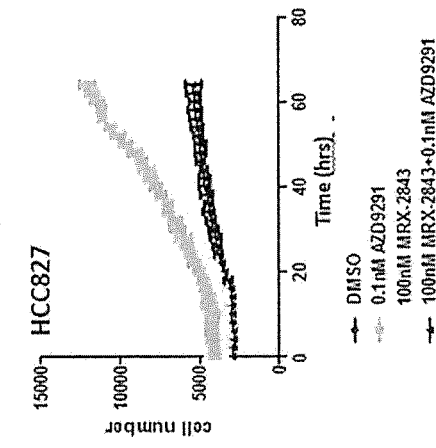
FIG. 9D
FIG. 9E
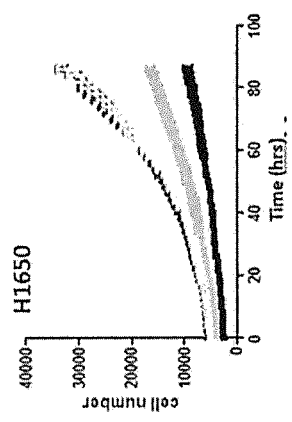
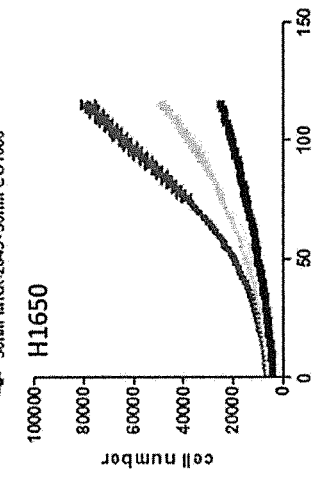

METHOD OF TREATING CANCER WITH A COMBINATION OF MER TYROSINE KINASE INHIBITOR AND AN EPIDERMAL GROWTH FACTOR RECEPTOR (EGFR) INHIBITOR

CROSS-REFERENCE TO RELATED APPLICATIONS

This application claims the benefit of U.S. Provisional Application No. 62/309,772, filed Mar. 17, 2016, the disclosure of which is incorporated herein by reference in its entirety.

FIELD OF THE INVENTION

The present invention concerns compounds, compositions and methods for the treatment of cancer.

BACKGROUND OF THE INVENTION

Lung cancer is the leading cause of cancer-related deaths with poor survival rate worldwide. Non-small cell lung cancer (NSCLC) accounts for 85% of all lung cancers and 60% of these have overexpression of wild-type EGFR (wtEGFR), which portends a poor prognosis. EGFR tyrosine kinase inhibitors (TKIs) have been effective for treatment of NSCLCs with activating EGFR mutations but not against NSCLCs with wtEGFR overexpression, indicating an urgent need for novel strategies to treat this class of tumors.

SUMMARY OF THE INVENTION

A first aspect of the present invention is a method of treating tumors in a mammalian subject in need thereof, comprising: concurrently administering to the subject a first active compound (e.g., a MER tyrosine kinase (MERTK) inhibitor) and (as a second active compound) an Epidermal Growth Factor Receptor (EGFR) inhibitor in a treatment-effective amount, with the first active compound administered to the subject in an amount effective to enhance the efficacy of the EGFR inhibitor in treating the tumors.

In some embodiments, the tumors comprise non-small cell lung cancer, glioblastoma, breast, head or neck, colon, gastric, or bladder cancer tumors.

In some embodiments, the tumors comprise non-small cell lung cancer tumors.

In some embodiments, the tumors comprise malignant primary tumors.

In some embodiments, the tumors comprise metastatic secondary tumors.

In some embodiments, the tumors comprise metastatic non-small cell lung cancer tumors in the brain.

In some embodiments, cells of the tumors over-express wild-type EGFR, and/or cells of the tumors express a mutant EGFR (e.g., the L858R activating mutant, the Exon 19 deletion activating mutant, the $\Delta$E746-A750 activating mutant, the T790M resistance mutant, etc.).

In some embodiments, the first active compound and the EGFR inhibitor are administered in a synergistic effective amount (e.g., sequentially in separate pharmaceutical carriers, or simultaneously in the same pharmaceutical carrier).

In some embodiments, the method results in one or more of: (a) inhibition of tumor growth; (b) reduction in tumor size; (c) reduction in the number of tumors, and (d) decreased tumor burden in the subject.

A further aspect of the invention is a pharmaceutical composition comprising: (a) a first active compound (e.g., a MERTK inhibitor; and (b) an Epidermal Growth Factor Receptor (EGFR) inhibitor as a second active compound; in (c) a pharmaceutically acceptable carrier (e.g., with the MERTK inhibitor and the EGFR inhibitor included in the carrier in an amount effective to treat tumors in a subject in need thereof; and with the MERTK inhibitor included in the carrier in an amount effective to enhance the efficacy of the EGFR inhibitor in treating the tumors.) The composition may be provided in oral dosage form (e.g., as a tablet or capsule). In some embodiments, the first active compound and the EGFR inhibitor are included in the composition in an amount having therapeutic synergy.

While in some embodiments of the methods of treating subjects described herein, a synergistic effect of the active agents on killing tumor cells may be obtained, in other embodiments an additive effect of the active agents on killing tumor cells is obtained, but with less than additive toxic effect on normal or healthy cells of that subject. In another aspect, the synergistic effect is reduction or prevention of resistance developing in the subject to one or the other, or both of, the active agents, after repeated treatment. In still other embodiments, the present invention provides a beneficial effect, such as an additive effect, on treating or killing tumor cells of a type that has been otherwise resistant to treatment (e.g., metastatic lung cancer tumors in the brain), with or without less than additive toxic effect on normal or healthy cells of the subject.

BRIEF DESCRIPTION OF THE FIGURES

FIG. 5A is an immunoblot showing decreased MERTK expression mediated by shRNA in A549 cells. FIG. 5B shows A549 and A549 shMERTK cells treated with CO-1686 or vehicle and confluence was quantified using the Incucyte ZOOM® live cell imaging system. Treatment with CO-1686 resulted in a more substantial reduction in cell number in the A549 shMERTK cell line (23.4±0.22%) compared to wild-type A549 cells (9.9±2.89%).

FIG. 6A is an immunoblot showing decreased EGFR expression mediated by siRNA in A549 and A549 shMERTK cells. FIG. 6B shows A549 and A549 shMERTK cells treated with CO-1686 or vehicle and confluence was quantified using the Incucyte ZOOM® live cell imaging system. Inhibition of EGFR with siRNA resulted in a greater reduction in cell number in the A549 shMERTK cell line (30.9±3.02%) compared to wild-type A549 cells (3.2±1.22%).

FIGS. 9A-9E show that CO-1686 and AZD-9291 synergize with MRX-2843 in a broad spectrum of mutant EGFR NSCLC cell lines. For treatment with CO-1686, the cell lines are shown in FIG. 9A (H1650), FIG. 9B (H4006), and FIG. 9C (PC9). For treatment with AZD-9291, the cell lines are shown in FIG. 9D (H1650) and FIG. 9E (HCC827). The indicated NSCLC cell lines were treated with CO-1686, AZD-9291, and/or MRX-2843 and cells were counted every 2 hours.

FIG. 12C shows the cell lysates. The indicated proteins were detected by immunoblot.

DETAILED DESCRIPTION

Figure 1:
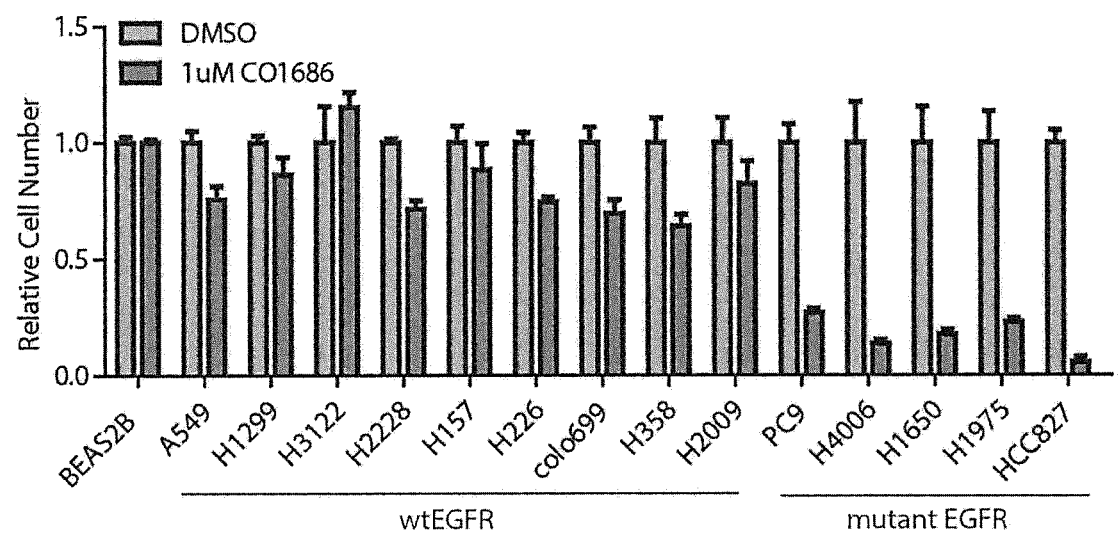
FIG. 1 shows wild-type EGFR cell lines are resistant to CO-1686 compared to mutant EGFR NSCLC cell lines. NSCLC and normal bronchial epithelial (BEAS2B) cell lines were cultured with CO-1686 for 60 hours and confluency was determined (BEAS2B) or cells were counted (NSCLC cell lines) and normalized to vehicle-controls.
Figure 2A:
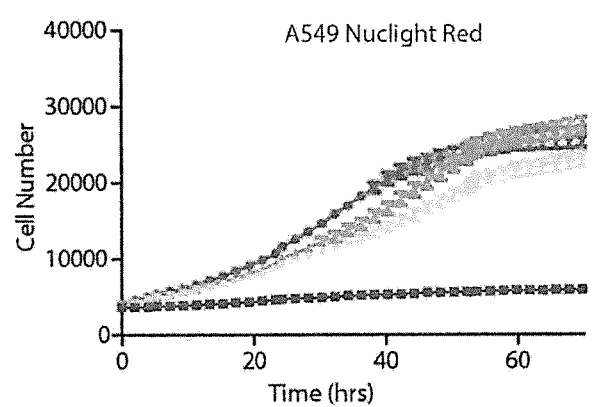
FIGS. 2A and 2B show that CO-1686 synergizes with MRX-2843 to inhibit A549 expansion in culture. A549 and BEAS2B cells were treated with CO-1686 and/or MRX-2843 and confluency was determined (BEAS2B) or Nuclight Red labeled cells were counted (A549 Nuclight Red) every 2 hrs. Combined treatment with CO-1686 and MRX-2843 resulted in dramatic synergistic growth inhibition in A549 cultures (FIG. 2A), but had no significant effect on BEAS2B, a normal human bronchial epithelial cell line (FIG. 2B).
Figure 2B:
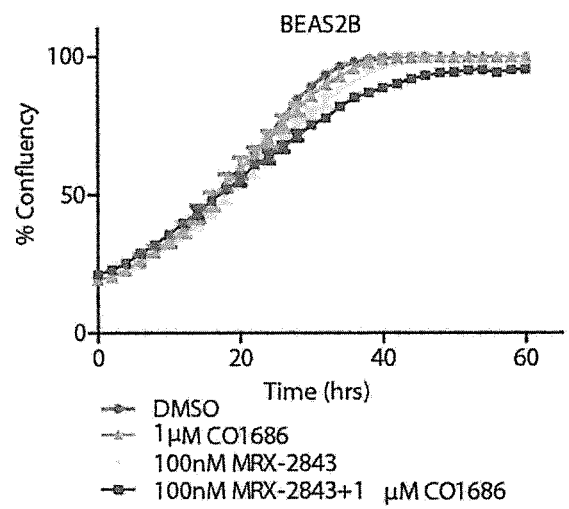
Figure 3:
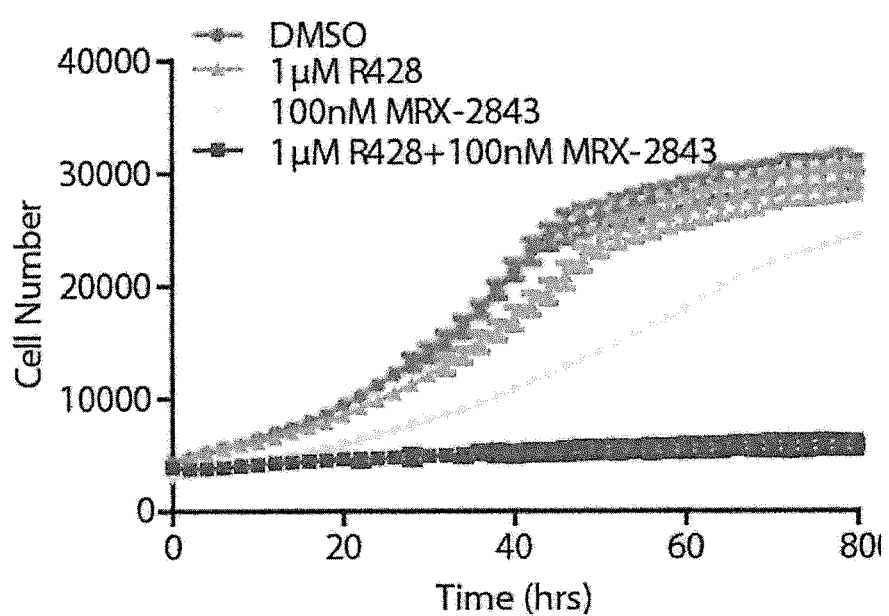
FIG. 3 shows that CO-1686 also synergized with the Axl inhibitor R428. A549 cells were treated with CO-1686 and/or MRX-2843 and Nuclight Red labeled cells were counted every 2 hrs.
Figure 4:
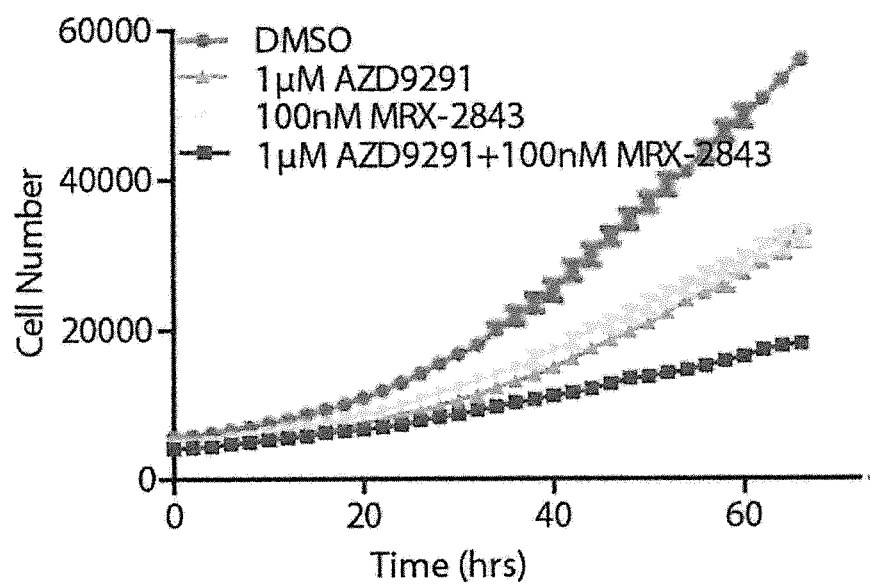
FIG. 4 shows that AZD-9291, a 3rd generation EGFR inhibitor, synergized with MRX-2843. A549 cells were treated with AZD-9291 and/or MRX-2843 and Nuclight Red cells were counted every 2 hrs.
Figure 5A:
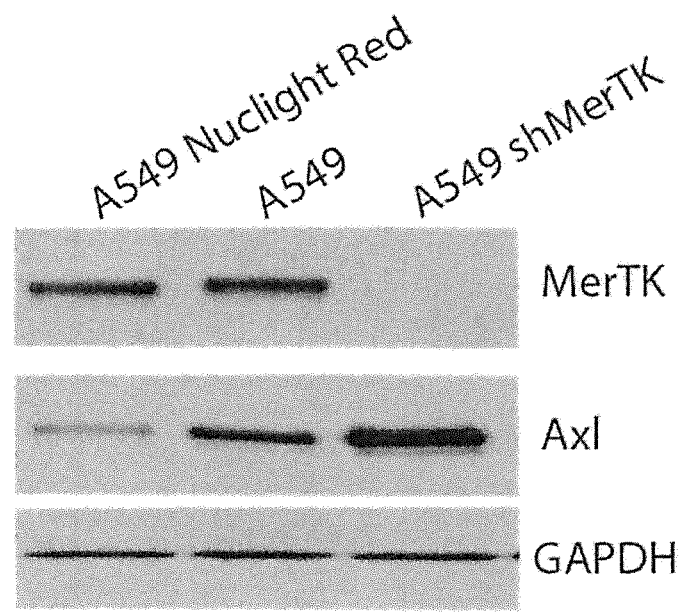
FIGS. 5A and 5B show inhibition of MERTK using shRNA sensitized A549 cells to CO-1686.
Figure 5B:
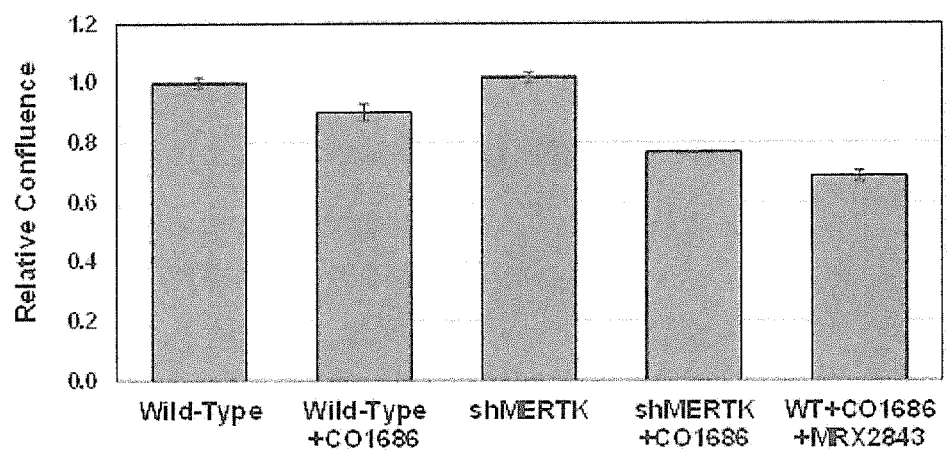
Figure 6A:
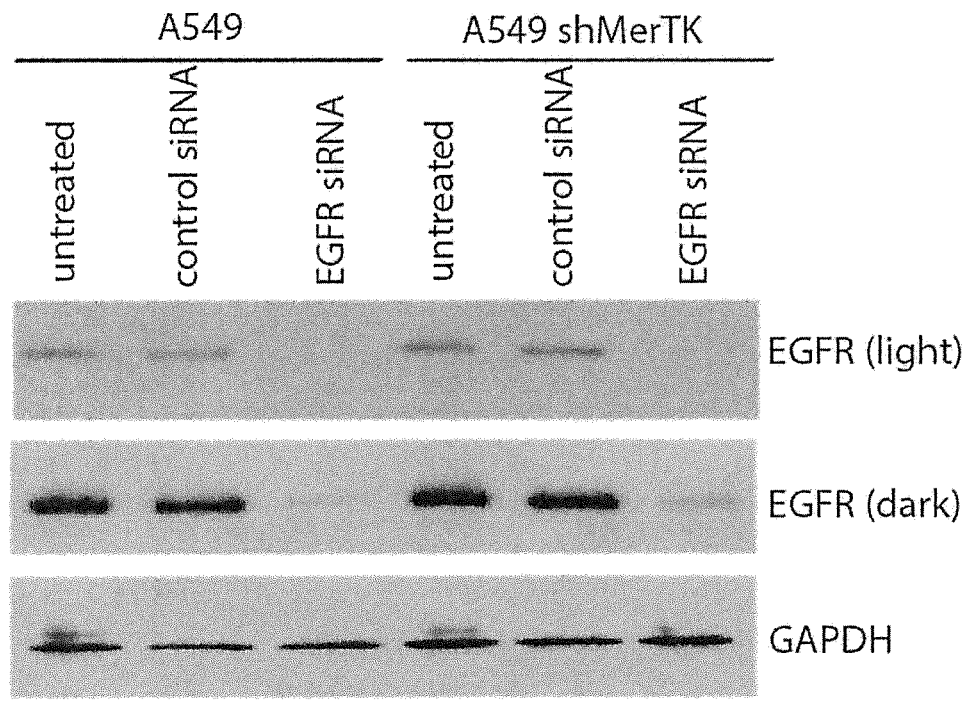
FIGS. 6A and 6B show inhibition of MERTK using shRNA sensitized A549 cells to siRNA-mediated EGFR inhibition and had a similar magnitude of effect relative to treatment with a MRX-2843.
Figure 6B:
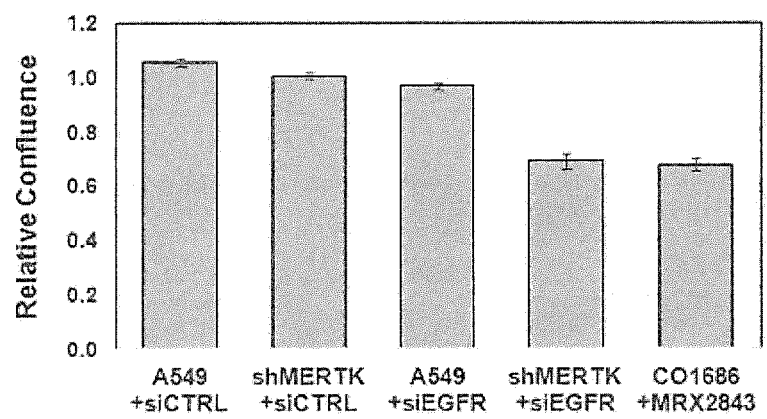
Figure 7:
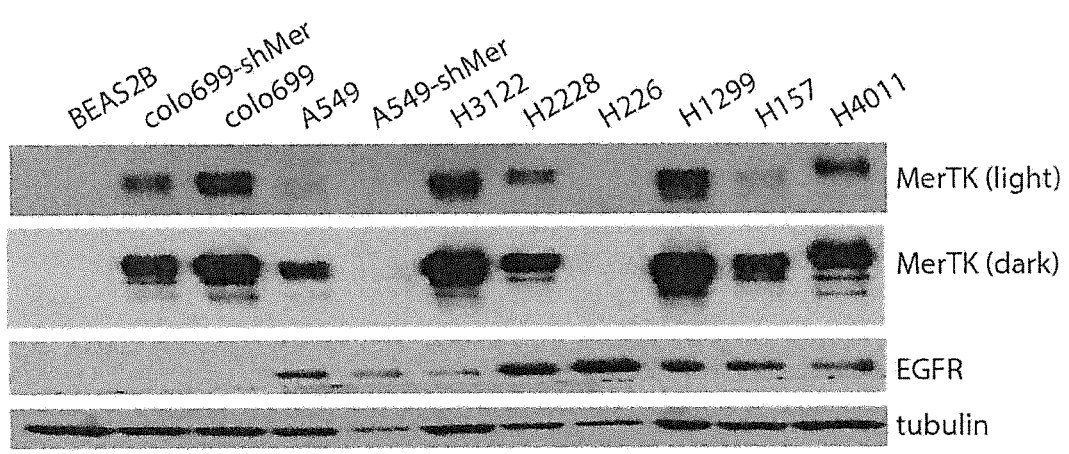
FIG. 7 shows that EGFR and MERTK are frequently aberrantly expressed in NSCLC cells. The immunoblots show expression of EGFR and MERTK proteins in NSCLC cell lines, but not in normal bronchial epithelial cells (BEAS2B).
Figure 8:
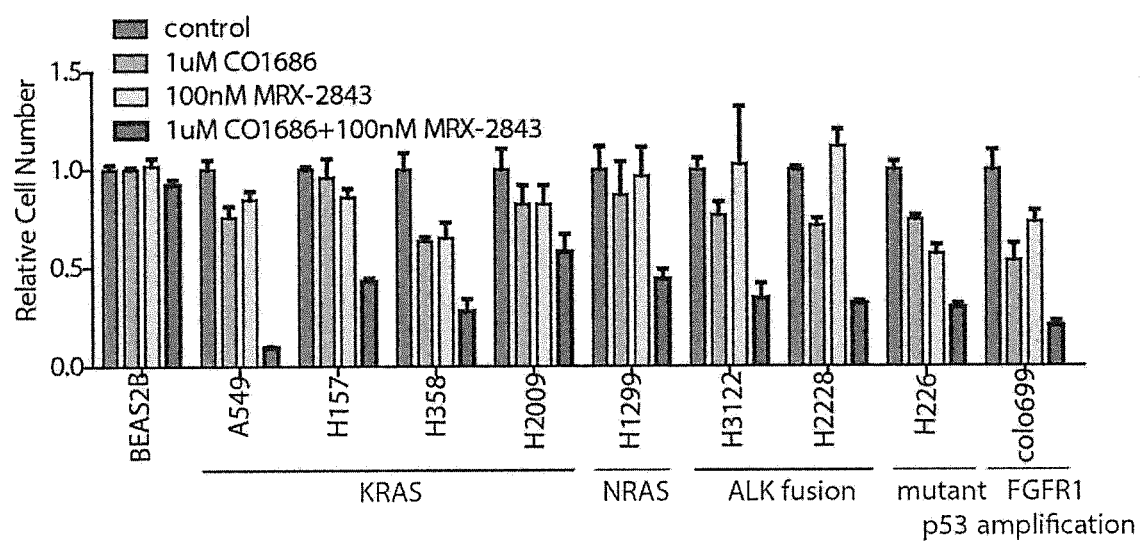
FIG. 8 shows that CO-1686 synergizes with MRX-2843 in a broad spectrum of wild-type EGFR NSCLC cell lines. The indicated NSCLC cell lines were treated with CO-1686 and/or MRX-2843 for 60 hours and cells were counted and normalized to vehicle controls.
Figure 10A:
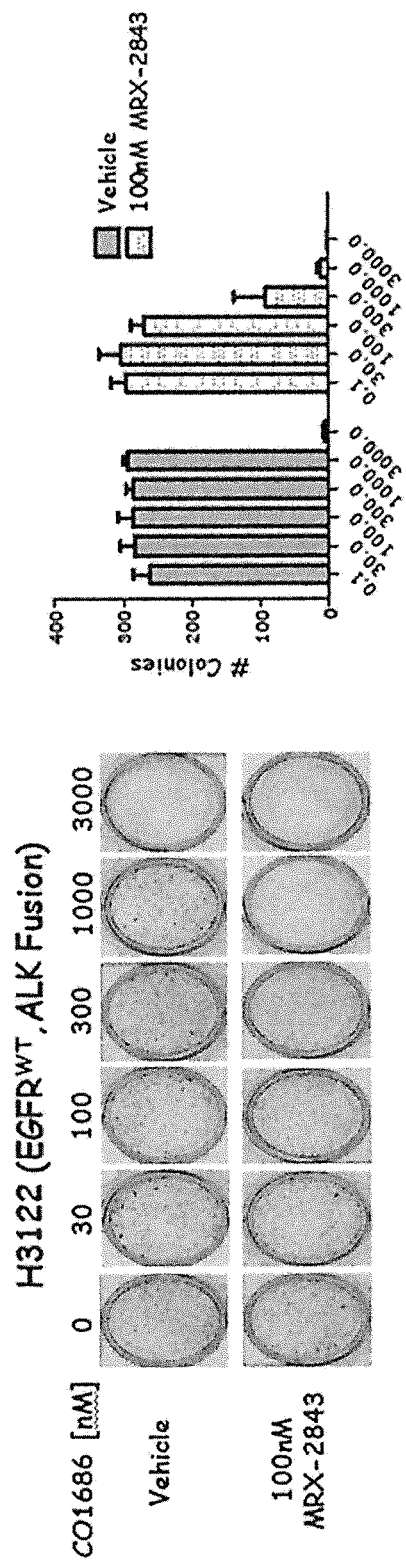
FIGS. 10A and 10B show that MRX-2843 and CO-1686 interact to provide greater inhibition of colony-forming potential in wild-type EGFR and mutant EGFR NSCLC cell lines. The indicated NSCLC cell lines in FIG. 10A (H3122) and FIG. 10B (PC9) were treated with CO-1686 and/or MRX-2843 for 8 days and then colonies were stained and counted.
Figure 10B:
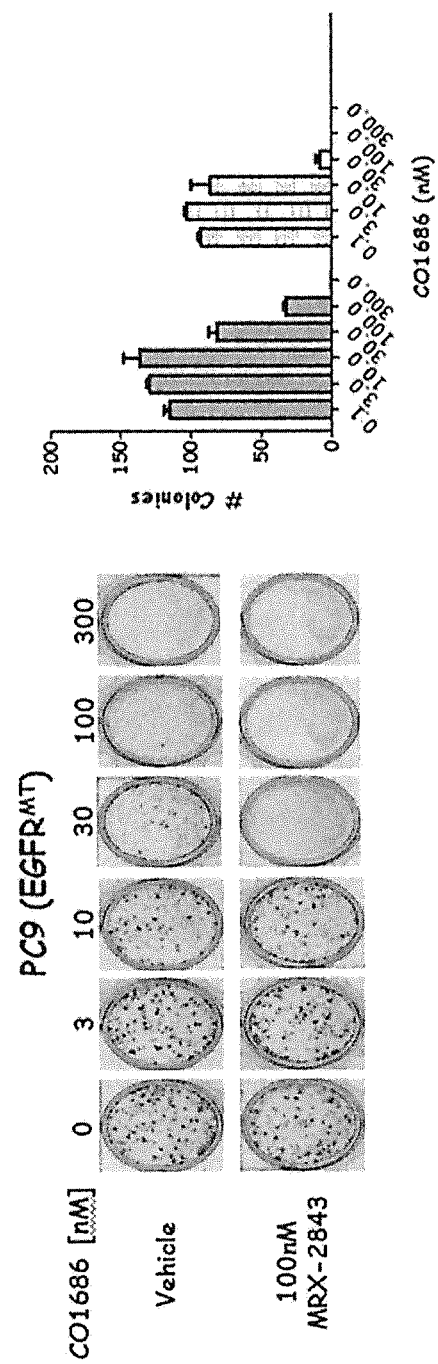
Figures 11A, 11B:
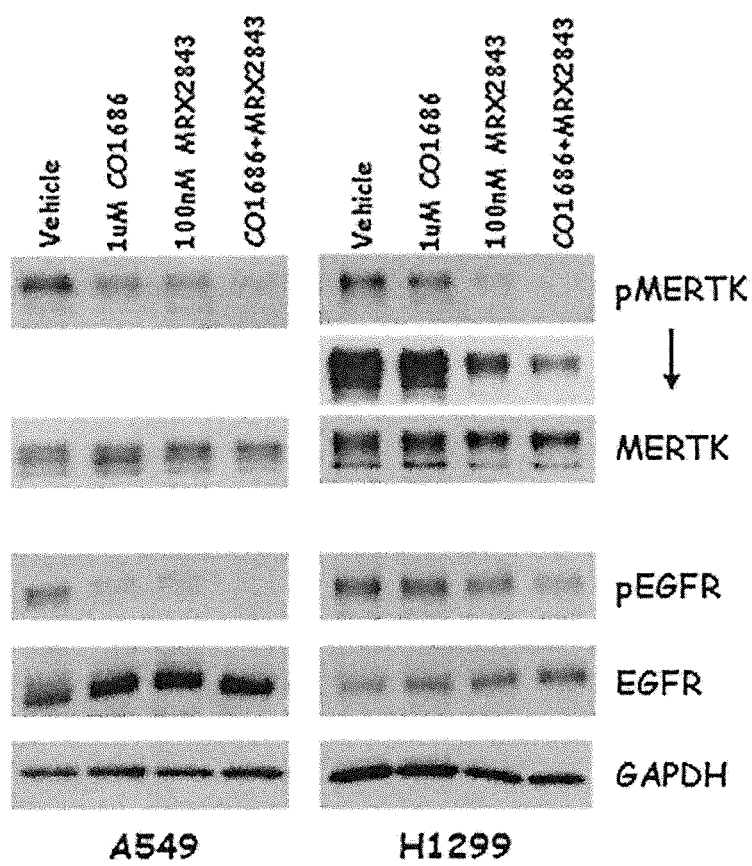
FIGS. 11A and 11B show that combined treatment with MRX-2843 and CO-1686 more potently inhibits phosphorylation of MERTK and EGFR compared to single agents in NSCLC cell lines. The indicated NSCLC cell lines in FIG. 11A (A549) and FIG. 11B (H1299) were treated with CO-1686 and/or MRX-2843. Cultures were treated with pervanadate phosphatase inhibitor to stabilize phosphorylated MERTK protein and MERTK was immunoprecipitated (top panels only). The indicated proteins were detected by immunoblot.
Figure 12A:
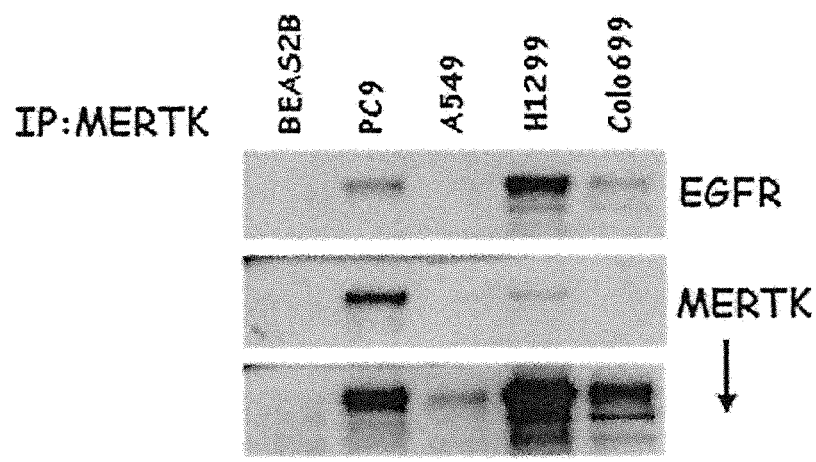
FIGS. 12A-C show that EGFR co-immunoprecipitates with MERTK and AXL. Cell lysates were prepared from the indicated NSCLC cell lines and MERTK (FIG. 12A) or AXL (FIG. 12B) were immunoprecipitated.
Figure 12B:
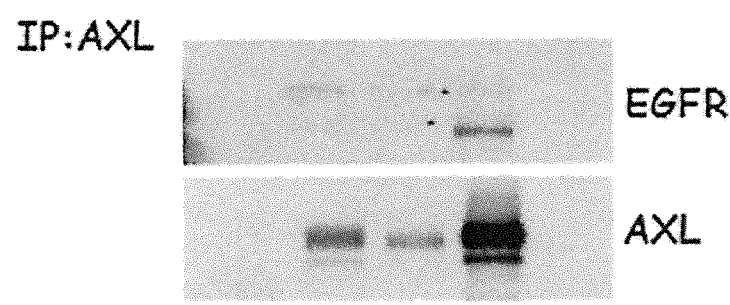
Figure 12C:
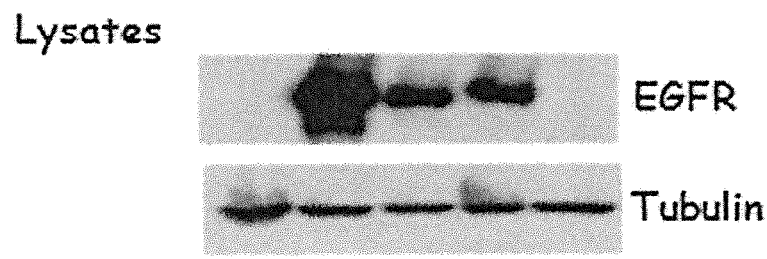
Figure 13:
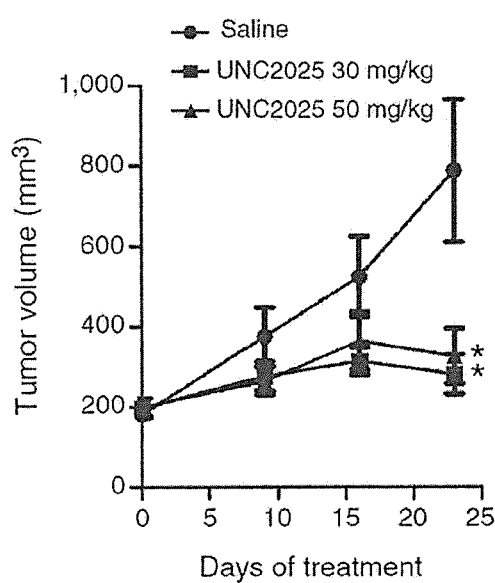
FIG. 13 shows tumor volume in mice with a subcutaneous xenograft of the A549 cell line treated with UNC2025, a MERTK inhibitor, or saline vehicle as reported previously in Cummings et al., *Mol. Cancer Ther.,* 2015, 14(9), 2014-2022.

The MERTK receptor tyrosine kinase is a potential therapeutic target in NSCLC. Novel MERTK-selective small molecule tyrosine kinase inhibitors (TKI) with favorable properties for clinical translation, such as MRX-2843 (Zhang, W., et al., *J. Med. Chem.,* 2014, 57(16):7031-41) have been developed. Irrespective of driver oncogene status, these MERTK TKIs have potent anti-tumor effects in cell culture models and inhibit tumor growth in xenografts of the wild-type EGFR-expressing A549 cell line.

A library screen was used to identify kinase inhibitors that enhance or synergize with MRX-2843 to inhibit expansion of the A549 cell line in culture. The screen identified CO-1686, a third-generation EGFR TKI currently in clinical trials, which enhances or synergizes with MRX-2843. While treatment with MRX-2843 or CO-1686 alone reduced A549 cells number by 13.2±4.1% ($p<0.05$) and 20.9±5.7% ($p<0.01$), respectively, treatment with MRX-2843 and CO-1686 together at these concentrations reduced cell number by 82.0±1.2%, ($p<0.0001$ compared with single treatment).

Synergistic inhibition was observed in multiple NSCLC cell lines with wild-type EGFR overexpression or an activating EGFR mutation and in response to combined treatment with another orally available EGFR TKI AZD-9291 (Cross, D. A., et al., *Cancer Discov.,* 2014, 4(9):1046-61). Also, R428, an Axl-selective inhibitor (Holland, S. J., et al., *Cancer Res,* 2010, 70(4):1544-54), synergized with CO-1686 to inhibit A549 expansion.

Biochemical studies demonstrated upregulation of EGFR in response to siRNA-mediated MERTK inhibition and co-immunoprecipitation of MERTK and EGFR, MERTK and AXL, and AXL and EGFR. Without being bound by theory, it is believed that EGFR, AXL and MERTK physically interact, thus providing multiple potential mechanisms for the synergistic anti-tumor effects mediated by combined MERTK or AXL and EGFR inhibition.

Taken together, the data provided herein reveal physical and functional interactions between MERTK, AXL and EGFR in NSCLC cell lines which provides a novel strategy for treatment of NSCLC with wild-type EGFR overexpression.

The present invention is explained in greater detail in the specification set forth below. The disclosures of all United States patent references cited herein are to be incorporated herein in their entirety.

1. Definitions

"Deuterium" as used herein alone or as part of another group, refers to a safe, non-radioactive relative of hydrogen.

Any hydrogen may be replaced with deuterium to modify/improve metabolic stability, resulting in better safety, tolerability and/or efficacy.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "lower alkyl" is intended to include both substituted and unsubstituted alkyl or lower alkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, acylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in lower alkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "lower alkenyl" is intended to include both substituted and unsubstituted alkenyl or lower alkenyl unless otherwise indicated and these groups may be substituted with groups as described in connection with alkyl and lower alkyl above.

"Alkynyl" as used herein alone or as part of another group, refers to a straight or branched chain hydrocarbon containing from 1 to 10 carbon atoms (or in lower alkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "lower alkynyl" is intended to include both substituted and unsubstituted alkynyl or lower alkynyl unless otherwise indicated and these groups may be substituted with the same groups as set forth in connection with alkyl and lower alkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or lower alkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and lower alkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or lower alkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Mercapto" as used herein refers to an —SH group.

"Azido" as used herein refers to an —$N_3$ group.

"Cyano" as used herein refers to a —CN group.

"Formyl" as used herein refers to a —C(O)H group.

"Carboxylic acid" as used herein refers to a —C(O)OH group.

"Hydroxyl" as used herein refers to an —OH group.

"Nitro" as used herein refers to an —$NO_2$ group.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Amino" as used herein means the radical —$NH_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —$NR_aR_b$, where $R_a$ and $R_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —$NR_aR_b$, where $R_a$ is an acyl group as defined herein and $R_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)$NR_aR_b$ radical, where $R_a$ and $R_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as amino, alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —S(O)$_2NR_aR_b$ radical, where $R_a$ and $R_b$ are any suitable substituent such as H, alkyl, cycloalkyl, alkenyl, alkynyl or aryl.

"Urea" as used herein alone or as part of another group refers to an —N($R_c$)C(O)$NR_aR_b$ radical, where $R_a$, $R_b$ and $R_c$ are any suitable substituent such as H, alkyl, cycloalkyl, alkenyl, alkynyl or aryl.

"Alkoxyacylamino" as used herein alone or as part of another group refers to an —N($R_a$)C(O)$OR_b$ radical, where $R_a$, $R_b$ are any suitable substituent such as H, alkyl, cycloalkyl, alkenyl, alkynyl or aryl.

"Aminoacyloxy" as used herein alone or as part of another group refers to an —OC(O)$NR_aR_b$ radical, where $R_a$ and $R_b$ are any suitable substituent such as H, alkyl, cycloalkyl, alkenyl, alkynyl or aryl.

"Polar group" as used herein refers to a group wherein the nuclei of the atoms covalently bound to each other to form the group do not share the electrons of the covalent bond(s) joining them equally; that is the electron cloud is denser about one atom than another. This results in one end of the covalent bond(s) being relatively negative and the other end relatively positive; i.e., there is a negative pole and a positive pole. Examples of polar groups include, without limitations, halo, hydroxy, alkoxy, carboxy, nitro, cyano, amino (primary, secondary and tertiary), amido, ureido, sulfonamido, sulfinyl, sulfhydryl, silyl, S-sulfonamido, N-sulfonamido, C-carboxy, O-carboxy, C-amido, N-amido, sulfonyl, N-tert-butoxycarbonyl (or "t-BOC") groups, phosphono, morpholino, piperazinyl, tetrazolo, and the like. See, e.g., U.S. Pat. No. 6,878,733, as well as alcohol, thiol, polyethylene glycol, polyol (including sugar, aminosugar, uronic acid), sulfonamide, carboxamide, hydrazide, N-hydroxycarboxamide, urea, metal chelates (including macrocyclic ligand or crown ether metal chelates). The polar group can be an ionic group.

"Ionic group" as used herein includes anionic and cationic groups, and includes groups (sometimes referred to as "ionogenic" groups) that are uncharged in one form but can be easily converted to ionic groups (for example, by protonation or deprotonation in aqueous solution). Examples include but are not limited to carboxylate, sulfonate, phosphate, amine, N-oxide, and ammonium (including quaternized heterocyclic amines such as imidazolium and pyridinium) groups. See, e.g., U.S. Pat. Nos. 6,478,863; 6,800,276; and 6,896,246. Additional examples include uronic acids, carboxylic acid, sulfonic acid, amine, and moieties such as guanidinium, phosphoric acid, phosphonic acid, phosphatidyl choline, phosphonium, borate, sulfate, etc.

"Linking group" as used herein are generally bivalent aromatic, aliphatic, or mixed aromatic and aliphatic groups. Thus linking groups include linear or branched, substituted or unsubstituted aryl, alkyl, alkylaryl, or alkylarylalkyl linking groups, where the alkyl groups are saturated or unsaturated, and where the alkyl and aryl groups optionally containing independently selected heteroatoms such as 1, 2, 3 or 4 heteroatoms selected from the group consisting of N, O, and S. In some embodiments, linking groups containing from 2 to 20 carbon atoms are preferred. Numerous examples of suitable linking groups are known, including but not limited to those described in, U.S. Pat. Nos. 8,247,572; 8,097,609; 6,624,317; 6,613,345; 6,596,935; and 6,420,377, the disclosures of which are incorporated by reference herein in their entirety.

In all embodiments, combinations of substituents and/or variables are permissible only if such combinations result in compounds that conform to a known valence for each atom.

"Treat" as used herein refers to any type of treatment that imparts a benefit to a patient afflicted with a disease, including improvement in the condition of the patient (e.g., in one or more symptoms), delay in the progression of the disease, delay in onset of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Concurrently" as used herein means sufficiently close in time to produce a combined effect (that is, concurrently may be simultaneously, or it may be two or more administration events occurring sequentially within a short time period before or after each other).

"Synergistic" as used herein refers to a therapeutic combination which is more effective than the additive effects of the two or more single agents. A determination of a synergistic interaction between two active compounds may, in some embodiments, be based on the results obtained from the assays described herein. The results of these assays can be analyzed using, for example, the Bliss additivity method, and/or the Chou and Talalay combination method and Dose-Effect Analysis with CalcuSyn software in order to obtain a Combination Index (Chou and Talalay, 1984, *Adv. Enzyme Regul.* 22:27-55), and/or other suitable programs or technique. In a non-limiting example, the program utilized may be that described by Chou and Talalay, in "New Avenues in Developmental Cancer Chemotherapy," Academic Press, 1987, Chapter 2. In some embodiments, Combination Index values less than 0.8 indicate synergy, in some embodiments values greater than 1.2 indicate antagonism, and in some embodiments values between 0.8 to 1.2 indicate additive effects. The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, or as two separate oral tablets or capsules taken at the same time, or close in time. In general, during alternation therapy, an effective dosage of each active ingredient is administered sequentially, i.e., serially, whereas in combination therapy, effective dosages of two or more active ingredients are administered together. In some examples, Combination effects are evaluated using both the BLISS independence model and the highest single agent (HSA) model (Lehar et al., *Molecular Systems Biology* 2007, 3:80). BLISS scores quantify degree of potentiation from single agents and a BLISS score>0 suggests greater than simple additivity. An HSA score>0 suggests a combination effect greater than the maximum of the single agent responses at corresponding concentrations. See, e.g., U.S. Pat. No. 9,150,549.

As used herein, the phrase "enhance the efficacy of said EGFR inhibitor" refers to increasing one or more of the inhibitor's activities to a measurable extent. This includes inhibition of the kinase's direct activity, i.e. phosphorylation (i.e. enhanced inhibitor activity is reflected by reduced phosphorylation of one or more of the kinase's substrates) or enhancing effects associated with the activity of the kinase inhibitor in a cell. The latter may include cell death, in which case cell death is enhanced. Enhanced activity may be qualitative or quantitative. Thus the inhibitor's activity may be improved 2, 3, 4, 5, 6, 7, 8, 9, 10, 20, 30, 40, 50 60, 70, 80 90, or 100 fold or more relative to its activity without enhancement. In relation to phosphorylation, enhanced activity may be reflected by a reduction in phosphorylation (when compared to a control experiment in which no inhibitor is added) of at least 10, 20, 30, 40, 50, 60, 70, 80 or 90% on one or more substrates of the kinase Enhancing may also include an increased inhibition of tumor growth, a greater reduction in tumor size; a greater reduction in the number of tumors, and a decreased tumor burden in the subject when compared to a control. In one embodiment, the level of enhancement is as least 20%, alternatively at least 30%, 40%, 50%, 60%, 70%, 80%, 90%, 100%, 120%, 150%, or 200%. The manner of measuring this enhancement is known to one of ordinary skill in the art.

Enhancement may also refer to the ability to treat different cell lines which are resistant to the kinase inhibitor without enhancement. Further, enhancement may refer to the ability to prevent development of resistance associated with EGFR TKI monotherapy treatment. For example, EGFR resistant cell lines may be responsive following treatment with EGFR inhibitors whose efficacy has been enhanced Enhancement may further refer to the ability of the combinations described herein to treating or killing tumor cells of a type that has been otherwise resistant to treatment (e.g., metastatic lung cancer tumors in the brain), with or without less than additive toxic effect on normal or healthy cells of the subject. This enhancement also allows improved therapy (e.g. in resistant patients) and the use of lower doses of the inhibitor. Thus, the improved efficacy of the kinase inhibitors allows an amount of inhibitor to be used which is not therapeutically effective when administered alone.

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes. Subjects may be of any age, including infant, juvenile, adolescent, adult, and geriatric subjects.

2. First Active Compounds

First active compounds (in some embodiments referred to herein as MER tyrosine kinase or MERTK inhibitors) include but are not limited to those described in U.S. Pat. No. 9,273,056 (UNC-Chapel Hill), the disclosure of which is incorporated by reference herein in its entirety. Thus, in some embodiments, the first active compound may be a compound of Formula I, IA, or IB:

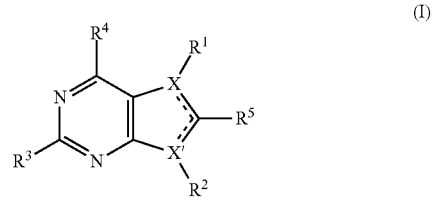

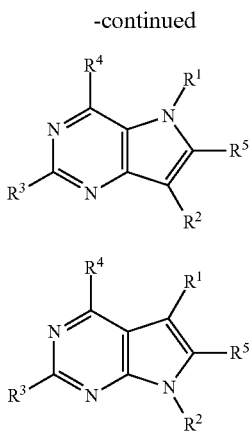

(IA)

(IB)

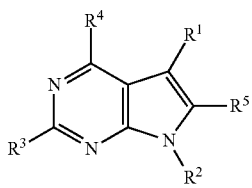

wherein:
one of X and X' is N and the other of X and X' is C;
one of the dashed lines is a single bond (between a ring carbon atom and a ring nitrogen atom) and the other of the dashed lines is a double bond (between two ring carbon atoms);
$R^1$ is aryl;
$R^2$ is —$R^{5'}R^6$, where $R^{5'}$ is a covalent bond or $C_{1-3}$ alkyl and $R^6$ is cycloalkyl, heterocycloalkyl, aryl, heteroaryl or alkyl, and wherein $R^6$ is optionally substituted from one to two times with independently selected polar groups;
$R^3$ is —$NR^7R^8$, where $R^7$ and $R^8$ are each independently selected from H, alkyl, arylalkyl; cycloalkylalkyl, heterocycloalkylalkyl, heteroaryalkyl, and alkoxyalkyl, each of which is optionally substituted one, two or three times with independently selected polar groups; and
$R^4$ is H, lower alkyl, halo, or lower alkoxy;
or a pharmaceutically acceptable salt or prodrug thereof.

In some embodiments of the foregoing, $R^1$ is phenyl or pyridyl, which phenyl or pyridyl is unsubstituted or substituted from 1 to 3 times with halo, amino, nitro, alkyl, alkoxyl, haloalkyl, cycloalkyl, heterocycloalkyl, aryl, or heteroaryl.

In some embodiments of the foregoing $R^{5'}$ is —$CH_2$—.

In some embodiments of the foregoing, $R^8$ is $C_{1-8}$ alkyl, $C_{3-8}$ cycloalkyl, or $C_{1-8}$ arylalkyl.

In some embodiments of the foregoing, $R^6$ is cyclohexyl.

In some embodiments of the foregoing, $R^6$ is substituted once with amino.

In some embodiments of the foregoing, $R^7$ is H.

In some embodiments of the foregoing, $R^8$ is lower alkyl.

In some embodiments of the foregoing, $R^4$ is H.

In some embodiments of the foregoing, $R^1$ is aryl, wherein the aryl is unsubstituted or substituted from 1 to 3 times with one or a combination of halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro, or cyano, where m=0, 1, 2 or 3, and wherein the alkyl or heterocycloalkyl-$S(O)_m$ can be substituted from 1 to 3 times with one or a combination of halo, alkyl, haloalkyl, or unsubstituted or substituted heterocycloalkyl, wherein the substituted heterocycloalkyl can be substituted from 1 to 3 times with one or a combination of halo, alkyl, or haloalky; or $R^1$ is heteroaryl, wherein the heteroaryl is unsubstituted or substituted from 1 to 3 times with one or a combination of halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano, where m=0, 1, 2 or 3, and wherein the alkyl or heterocycloalkyl-$S(O)_m$ can be substituted from 1 to 3 times with one or a combination of halo, alkyl, haloalkyl, or unsubstituted or substituted heterocycloalkyl, wherein the substituted heterocycloalkyl can be substituted from 1 to 3 times with one or a combination of halo, alkyl, or haloalkyl.

In some embodiments of the foregoing, $R^5$ is H, lower alkyl, halo, or lower alkoxy.

In some embodiments of the foregoing, $R^{5'}$ is a covalent bond or $C_{1-3}$ alkyl.

In some embodiments of the foregoing, $R^8$ is $C_{1-8}$ alkyl or $C_{1-8}$ arylalkyl.

Active compounds may be provided as pharmaceutically acceptable prodrugs, which are those prodrugs of the active compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention.

As used herein, the term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. Nos. 6,680,324 and 6,680,322.

The active compounds disclosed herein can, as noted above, be provided in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Active compounds as described herein can be prepared in accordance with known procedures, or variations thereof that will be apparent to those skilled in the art.

3. EGFR Inhibitor Active Compounds

EGFR inhibitors useful for carrying out the present invention are known. Examples include, but are not limited to, those described in U.S. Pat. Nos. 8,703,769; 8,609,354; and 8,334,293, and in U.S. Patent Application Publication Nos. U.S. 20150044220 and U.S. 20130189248, the disclosures of which are incorporated by reference herein in their entirety.

Particular examples of EGFR inhibitors useful for carrying out the present invention include, but are not limited to: (a) the small organic molecule EGFR inhibitors gefitinib, erlotinib, lapatinib, Brigatinib (AP26113), Afatinib (BIBW2992), Neratinib (HKI-272), AZD3759, AZ5104, CL-387785 (EKI-785), Canertinib (CI-1033), Poziotinib (HM781-36B), Osimertinib (AZD-9291), PD168393, CNX-2006, Rociletinib (CO-1686, AVL-301), WZ4002, Pelitinib (EKB-569), AC480 (BMS-599626), TAK-285, CUDC-101, AEE788 (NVP-AEE788), CP-724714, Dacomitinib (PF299804, PF299), AG-490 (Tyrphostin B42), AST-1306, OSI-420, WHI-P154, WZ3146, WZ8040, AZD8931 (Sapitinib), PD153035 HCl, Icotinib, Varlitinib, AZD-9291, AEE788 (NVP-AEE 788), AG-1478 (NSC 693255), AG-490, Anlotinib, ARRY-380, BIBX 1382, and BMS-690514; and (b) the monoclonal antibody EGFR inhibitors cetuximab, panitumumab, zalutumumab, nimotuzumab, and matuzumab.

In some embodiments, the EGFR inhibitor can be one of those described in U.S. Pat. No. 8,975,249 (Celgene Avilomics), the disclosure of which is incorporated by reference herein in its entirety. For example, in some embodiments, the EGFR inhibitor has the structure of Formula XI:

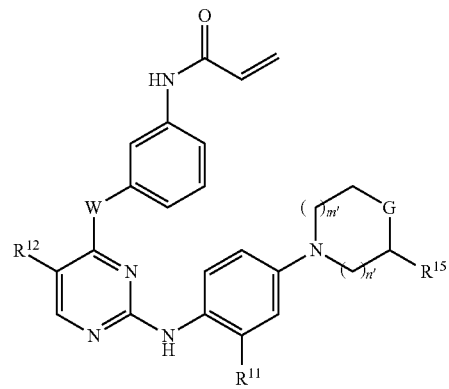

(XI)

wherein:

n' is 0, 1, or 2 (preferably 1);

m' is 0, 1, or 2 (preferably 1), wherein m' and n' are not simultaneously 0;

W is —O— or —NH— (preferably, W is —NH—);

$R^{11}$ is —$OR^{10}$;

each $R^{10}$ is independently $C_{1-4}$ alkyl or $C_{1-4}$ fluoroalkyl;

$R^{12}$ is —$CF_3$, Cl, or Br (preferably, $R^{12}$ is —$CF_3$);

G is —O—, —$NR^{13}$—, —$S(O_2)$—, or —$CH(OR^{14})$—, (preferably, G is —$NR^{13}$—);

$R^{13}$ is —C(O)—$R^{10}$, —C(O)$OR^{10}$, —C(O)$NHR^{10}$, —$SO_2$—R, —$SO_2NH_2$, —C(O)—$C_{1-4}$ alkylene-OH or —$SO_2$—$C_{1-4}$ alkylene-OH;

$R^{14}$ is hydrogen, $C_{1-4}$ alkyl, or $C_{1-4}$ fluoroalkyl; and $R^{15}$ is hydrogen or —C(O)$OR^{10}$;

or a pharmaceutically acceptable salt thereof.

In some embodiments, the compound of Formula XI has the structure:

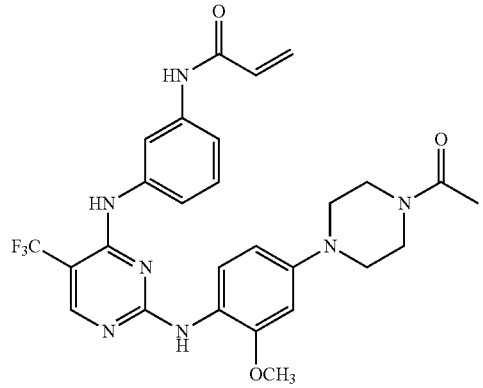

CO-1686 or a pharmaceutically acceptable salt thereof.

In other embodiments, the EGFR inhibitor can be one of those described in U.S. Pat. No. 8,946,235 (AstraZeneca), the disclosure of which is incorporated by reference herein in its entirety. For example, the EGFR inhibitor can have the structure of Formula XII:

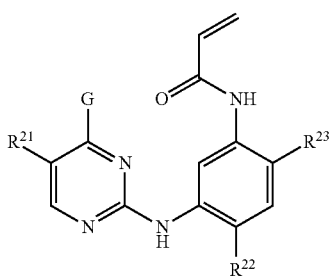

(XII)

wherein:

G is selected from 4,5,6,7-tetrahydropyrazolo[1,5-a]pyridin-3-yl, 1H-indol-3-yl, 1-methyl-1H-indol-3-yl and pyrazolo[1,5-a]pyridin-3-yl;

$R^{21}$ is selected from hydrogen, fluoro, chloro, methyl and cyano;

$R^{22}$ is selected from methoxy and methyl; and $R^{23}$ is selected from (3R)-3-(dimethylamino)pyrrolidin-1-yl, (3S)-3-(dimethyl-amino)pyrrolidin-1-yl, 3-(dimethylamino)azetidin-1-yl, [2-(dimethylamino)ethyl]-(methyl)amino, [2-(methylamino)ethyl](methyl)amino, 5-methyl-2,5-diazaspiro[3,4]oct-2-yl, (3 aR,6aR)-5-methylhexa-hydropyrrolo[3,4-b]pyrrol-1 (2H)-yl, 1-methyl-1,2,3,6-tetrahydropyridin-4-yl, 4-methylpiperizin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-aminopropanoyl]piperazin-1-yl;

or a pharmaceutically acceptable salt thereof.

In some embodiments of the foregoing, the EGFR inhibitor has the structure:

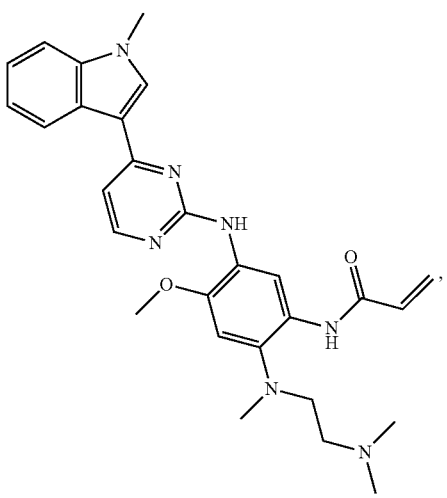

AZD9291 or a pharmaceutically acceptable salt thereof.

Numerous additional examples of EGFR inhibitors that can be used are also available, as noted above.

4. Pharmaceutical Formulations

The first active compound described in section 1 above (e.g., compounds of Formulas I, IA, and IB) and the EGFR inhibitor active compounds described in section 2 above (e.g., compounds of Formulas XI and XII) may be formulated for administration separately or together in the same pharmaceutical carrier in accordance with known techniques. See, e.g., Remington, *The Science And Practice of Pharmacy* (9$^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces), transdermal administration, and intraventricular injection (injection into a ventricle of the brain, e.g., by an implanted catheter or omman reservoir, such as in the case of morbid obesity) and although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

5. Dosage and Routes of Administration

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.001 µg/kg and about 1000 mg/kg of each active compound will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg of each active compound may be employed for oral administration. In some embodiments, a dosage from about 0.5 mg/kg to 5 mg/kg of each active compound may be employed for intramuscular injection. In some embodiments, dosages are 1 µmol/kg to 50 µmol/kg, and more preferably 22 µmol/kg and 33 µmol/kg of each active compound for intravenous or oral administration. The duration of the treatment can be once per day for a period of two to three weeks or until the condition is essentially controlled.

In some embodiments, the compound is administered to the subject at a dose of between about 0.001 µg/kg and about 1000 mg/kg, including but not limited to about 0.001 µg/kg, 0.01 µg/kg, 0.05 µg/kg, 0.1 µg/kg, 0.5 µg/kg, 1 µg/kg, 10 µg/kg, 25 µg/kg, 50 µg/kg, 100 µg/kg, 250 µg/kg, 500 µg/kg, 1 mg/kg, 5 mg/kg, 10 mg/kg, 25 mg/kg, 50 mg/kg, 100 mg/kg, and 200 mg/kg. As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller rangers is also encompassed, subject to any specifically excluded limit in the stated range. Where the stated range includes one or both of the limits, ranges excluding either or both of those included limits are also included.

The present invention is explained in greater detail in the following non-limiting Examples.

EXAMPLES

Example 1. Screening Assay Overview

Screening was carried out with 100 nM MRX-2843 and a 1 µM kinase library. The relative numbers of A549 cells were quantitated over time using the Incucyte ZOOM©® Live Cell Imaging system and library compounds that provided therapeutic benefit greater than the library compound alone were identified, including CO-1686. CO-1686 (Walter, A. O., et al., *Cancer Discov,* 2013. 3(12): p. 1404-15) is an irreversible and orally delivered 3rd generation EGFR kinase inhibitor that specifically targets the mutant forms of EGFR including T790M ($IC_{50}$=21 nM). Results are given in FIGS. 1-8.

Example 2. MERTK Inhibitor Combination Therapies

NSCLC cells were cultured in the presence of the indicated compound(s) or an equivalent volume of vehicle (DMSO) only and the numbers of viable cells were counted at the indicated intervals using the Incucyte ZOOM live cell imaging system. Results are given in FIGS. 14-16.

Figure 14:
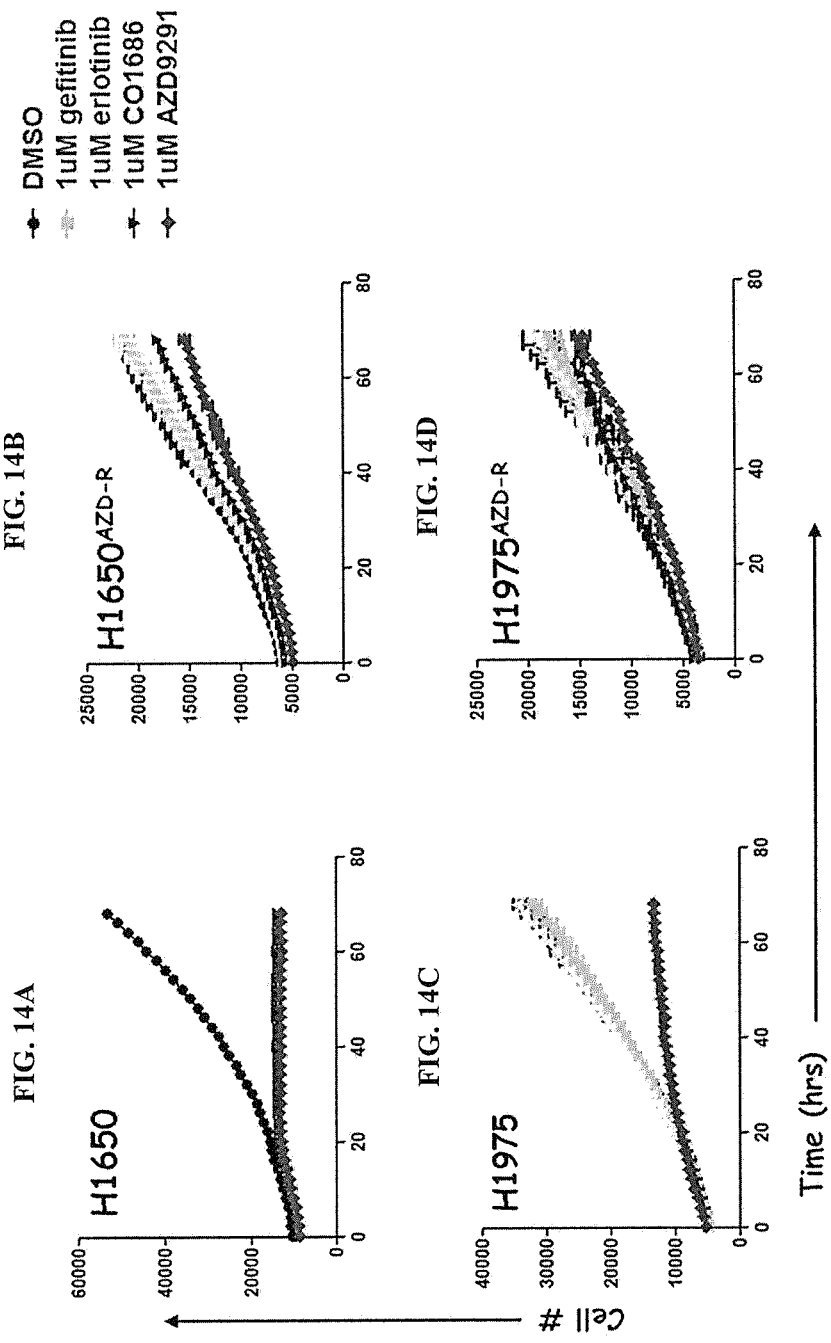
FIGS. 14A and 14B show mutant EGFR AZD-9291-resistant NSCLC cell lines are cross-resistant to other EGFR TKIs. The indicated cell lines are shown in FIG. 14A (H1650), FIG. 14B (H1650$^{AZD-R}$), FIG. 14C (H1975), and FIG. 14D (H1975$^{AZD-R}$).

As shown in FIG. 14, two different AZD-9291-sensitive NSCLC cell lines with known EGFR mutations were cultured in medium containing gradually increasing concentrations of AZD-9291 (osimertinib). Thus, derivative cell lines resistant to treatment with AZD-9291 alone were selected. Even though these lines (denoted by the AZD-R superscript) were selected for resistance to AZD-9291, they were cross-resistant to other first and second generations EGFR TKIs.

Figure 15:
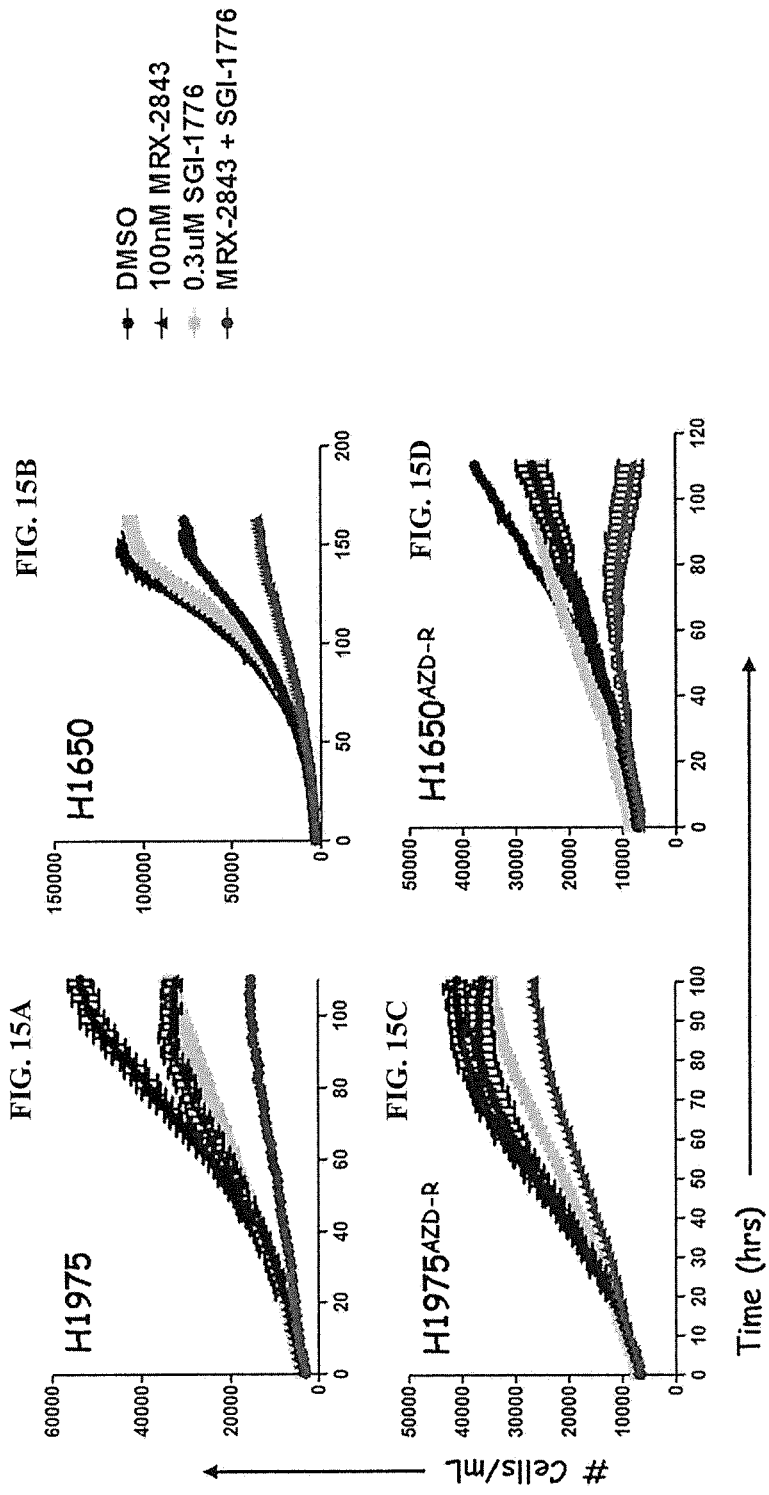
FIGS. 15A-15D show that SGI-1776 (which targets PIM kinase) and MRX-2843 mediate synergistic anti-tumor activity in mutant EGFR NSCLC cells & EGFR TKI-resistant derivatives. The indicated cell lines are shown in FIG. 15A (H1975), FIG. 15B (H1650), FIG. 15C (H1975$^{AZD-R}$), and FIG. 15D (H1650$^{AZD-R}$).
Figure 16:
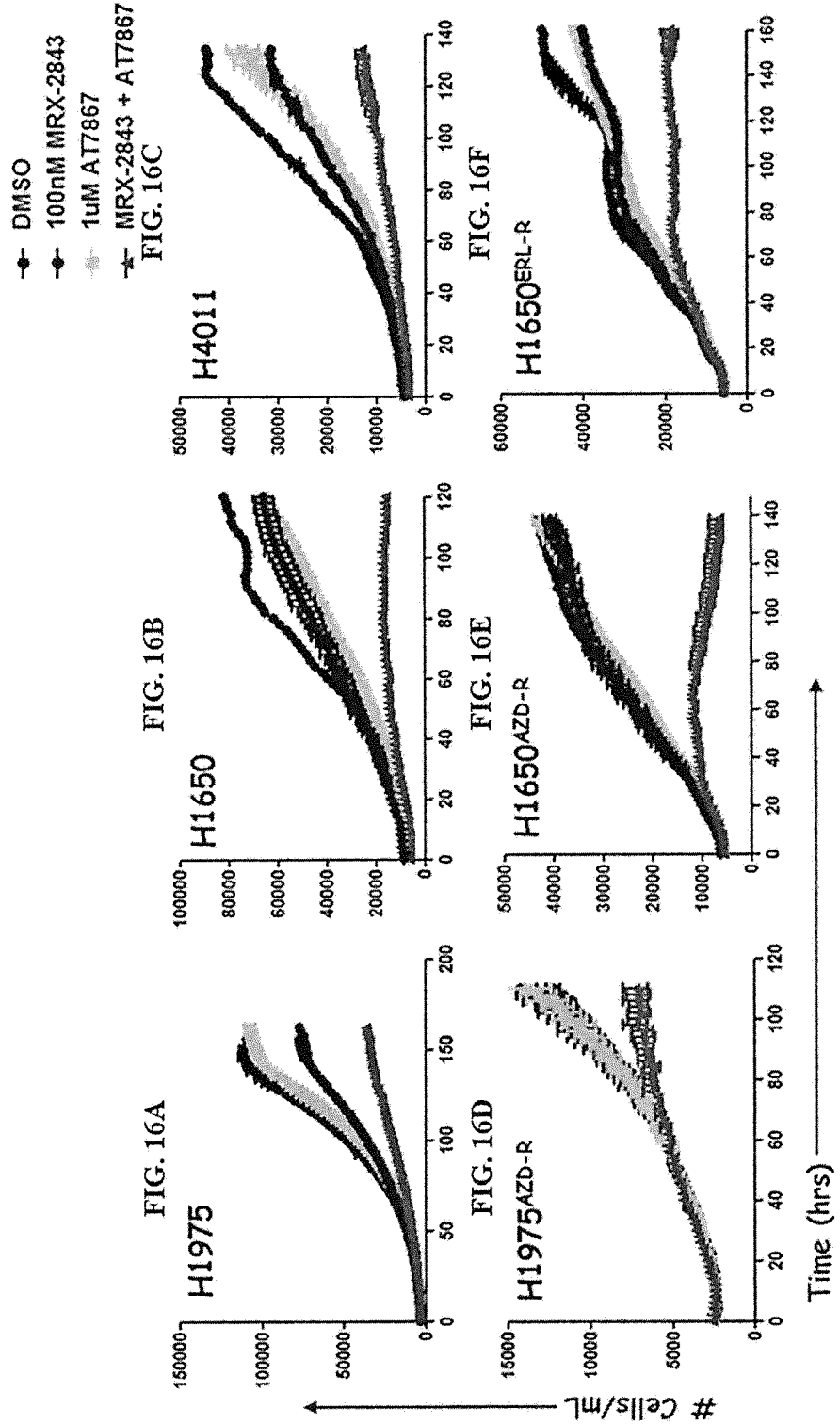
FIGS. 16A-16E show that AT7867 (which targets AKT and S6 kinases) and MRX-2843 mediate synergistic anti-tumor activity in mutant EGFR NSCLC cells & EGFR TKI-resistant derivatives. The indicated cell lines are shown in FIG. 16A (H1975), FIG. 16B (H1650), FIG. 16C (H4011), FIG. 16D (H1975$^{AZD-R}$), FIG. 16E (H1650$^{AZD-R}$), and FIG. 16F (H1650$^{ERL-R}$).
Figure 17:
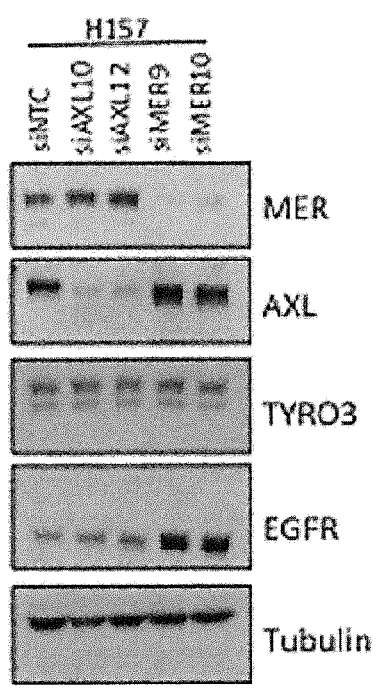
FIG. 17 shows inhibition of MERTK increases expression of EGFR in H157 NSCLC cells. The H157 wild-type EGFR NSCLC cells were transfected with one of two different siRNAs directed against MERTK (siMER9 and siMER10). MERTK and EGFR protein expression was determined by immunoblot.

As shown in FIGS. 15 and 16, two additional agents may combine with MRX-2843 to mediate more effective reduction in tumor cell number in mutant EGFR cell lines when compared to the agents by themselves. One agent is a PIM kinase inhibitor (SGI-1776, FIG. 15) and the other is an AKT/S6 kinase inhibitor (AT7867, FIG. 16). The combination effect was observed in both mutant EGFR cell lines and in AZD-9291 or erlotinib resistant derivative cell lines. Thus, inhibition using a combination of a MERTK kinase inhibitor and a PIM kinase inhibitor can be effective in treatment of patients who relapse on EGFR TKI therapy. Additionally, inhibition using a combination of a MERTK kinase inhibitor and an AKT/S6 kinase inhibitor can be effective in treatment of patients who relapse on EGFR TKI therapy.

In embodiments, the subject matter described herein is directed to treatment of a mutant EGFR NSCLC or TKI-resistant tumor with a MERTK tyrosine kinase inhibitor in combination with a PIM kinase inhibitor, an AKT kinase inhibitor, or a S6 kinase inhibitor.

The subject matter described herein further includes the following embodiments.

In an embodiment, a method of treating tumors in a mammalian subject in need thereof, comprising:

concurrently administering to the subject a first active compound (e.g., a MER tyrosine kinase (MERTK) inhibitor) and an Epidermal Growth Factor Receptor (EGFR) inhibitor in a treatment-effective amount, with the first active compound administered to the subject in an amount effective to enhance the efficacy of the EGFR inhibitor in treating the tumors.

As in any embodiment above, a method wherein the tumors comprise non-small cell lung cancer, glioblastoma, breast, head or neck, colon, gastric, or bladder cancer tumors.

As in any embodiment above, a method wherein the tumors comprise non-small cell lung cancer tumors.

As in any embodiment above, a method wherein the tumors comprise malignant primary tumors.

As in any embodiment above, a method wherein the tumors comprise metastatic secondary tumors.

As in any embodiment above, a method wherein the tumors comprise metastatic non-small cell lung cancer tumors in the brain.

As in any embodiment above, a method wherein
cells of the tumors over-express wild-type EGFR, and/or
cells of the tumors express a mutant EGFR (e.g., the L858R activating mutant, the Exon 19 deletion activating mutant, the ΔE746-A750 activating mutant, the T790M resistance mutant, etc.).

As in any embodiment above, a method wherein the first active compound and the EGFR inhibitor are administered in a synergistic effective amount (e.g., sequentially in separate pharmaceutical carriers, or simultaneously in the same pharmaceutical carrier).

As in any embodiment above, a method wherein the subject is human.

As in any embodiment above, a method wherein the method results in one or more of: (a) inhibition of tumor growth; (b) reduction in tumor size; (c) reduction in the number of tumors, and (d) decreased tumor burden in the subject.

As in any embodiment above, a method wherein the first active compound comprises a compound of Formula I:

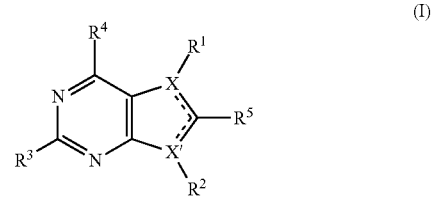

wherein:
one of X and X' is N and the other of X and X' is C;
one of the dashed lines in Formula I is a single bond and the other of the dashed lines in Formula I is a double bond;
$R^1$ is aryl, wherein the aryl is unsubstituted or substituted from 1 to 3 times with one or a combination of halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, halo alkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocycle-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano, where m=0, 1, 2 or 3, and wherein the alkyl or heterocycloalkyl-S(O)$_m$ can be substituted from 1 to 3 times with one or a combination of halo, alkyl, haloalkyl, or unsubstituted or substituted heterocycloalkyl, wherein the substituted heterocycloalkyl can be substituted from 1 to 3 times with one or a combination of halo, alkyl, or haloalky; or R$^1$ is heteroaryl, wherein the heteroaryl is unsubstituted or substituted from 1 to 3 times with one or a combination of halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano, where m=0, 1, 2 or 3, and wherein the alkyl or heterocycloalkyl-S(O)$_m$ can be substituted from 1 to 3 times with one or a combination of halo, alkyl, haloalkyl, or unsubstituted or substituted heterocycloalkyl, wherein the substituted heterocycloalkyl can be substituted from 1 to 3 times with one or a combination of halo, alkyl, or haloalkyl;

R$^2$ is —R$^{5'}$R$^6$, where R$^{5'}$ is a covalent bond or C1 to C3 alkyl and R$^6$ is cycloalkyl, and wherein R$^6$ is optionally substituted from one to two times with independently selected polar groups;

R$^3$ is —NR$^7$R$^8$, where R$^7$ and R$^8$ are each independently selected from H, alkyl, arylalkyl, cycloalkylalkyl, heterocycloalkylalkyl, heteroarylalkyl, and alkoxyalkyl, each of which is optionally substituted one, two or three times with independently selected polar groups;

R$^4$ is H, lower alkyl, halo, or lower alkoxy; and

R$^5$ is H, lower alkyl, halo, or lower alkoxy;

or a pharmaceutically acceptable salt thereof.

As in any embodiment above, a method wherein the compound of Formula I having the structure of Formula IA:

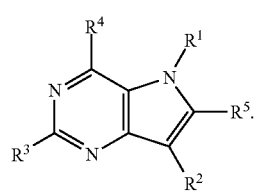

(IA)

As in any embodiment above, a method wherein the compound of Formula I having the structure of Formula IB:

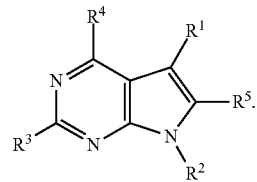

(IB)

As in any embodiment above, a method wherein R$^{5'}$ of the compound of Formula I is a covalent bond or C1 to C3 alkyl.

As in any embodiment above, a method wherein R$^1$ of said compound of Formula I is phenyl, or pyridyl, which phenyl or pyridyl is unsubstituted or substituted from 1 to 3 times with halo, amino, nitro, alkyl, alkoxyl, haloalkyl, cycloalkyl, heterocycloalkyl, aryl, or hetero aryl.

As in any embodiment above, a method wherein R$^8$ of the compound of Formula I is C1-C8 alkyl, or C1-C8 arylalkyl.

As in any embodiment above, a method wherein R$^6$ of the compound of Formula I is cyclohexyl.

As in any embodiment above, a method wherein R$^7$ of the compound of Formula I is H and/or R$^4$ of the compound of Formula I is H.

As in any embodiment above, a method wherein the compound of Formula I has the structure:

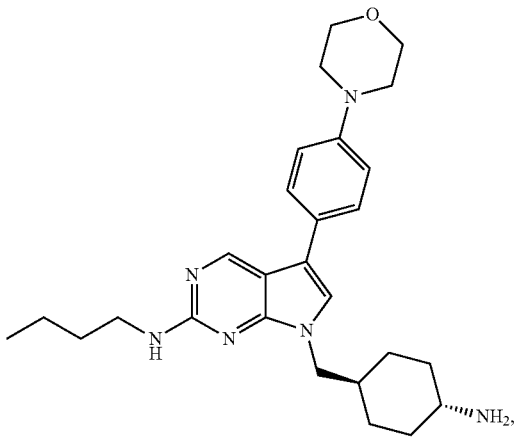

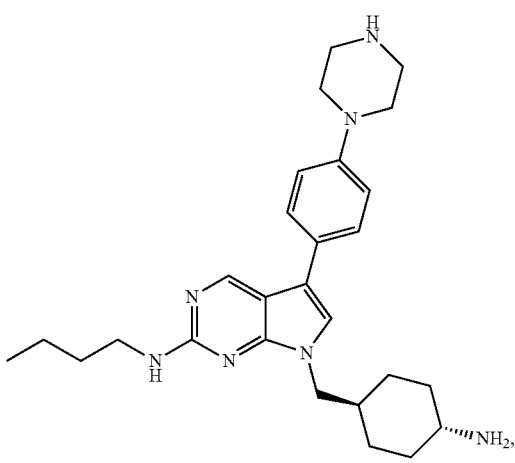

23
-continued
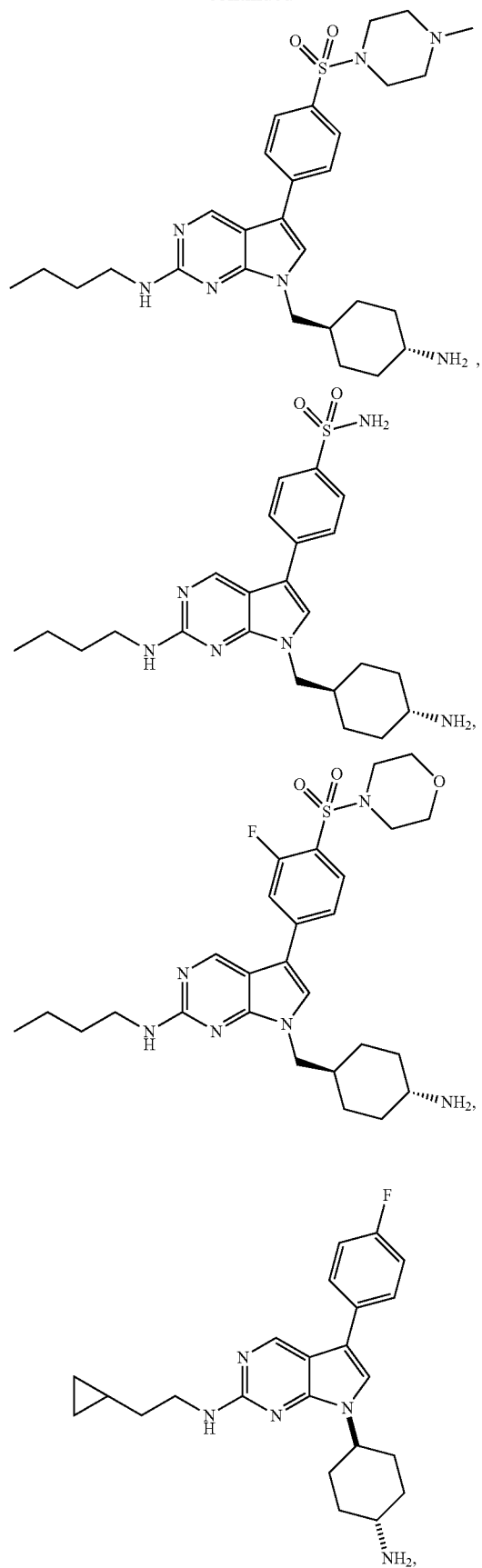
24
-continued
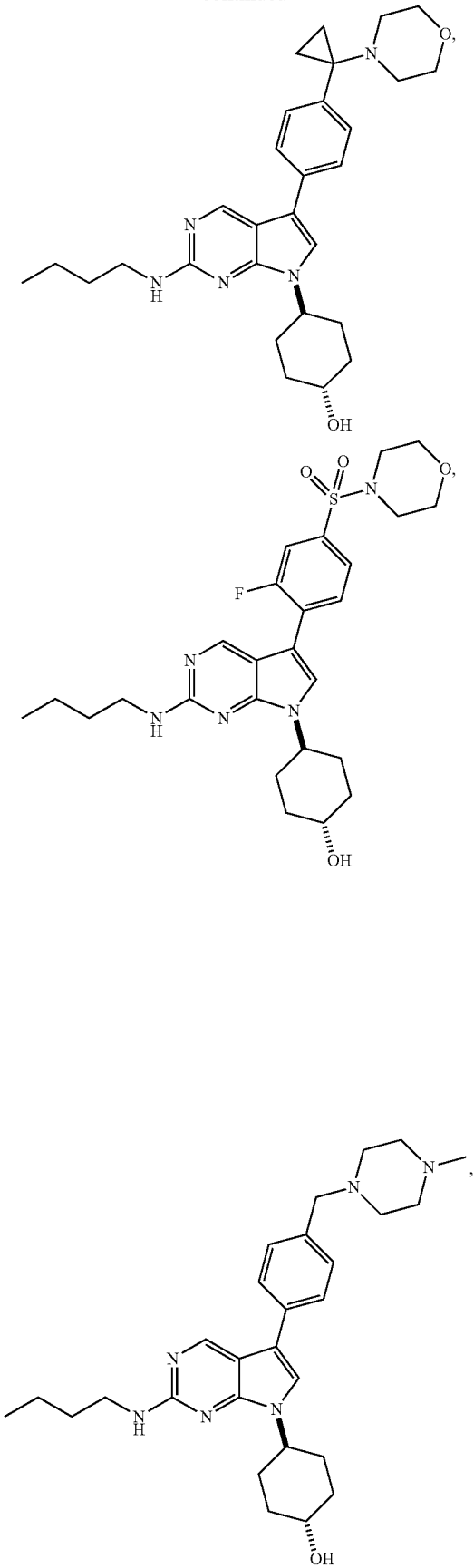

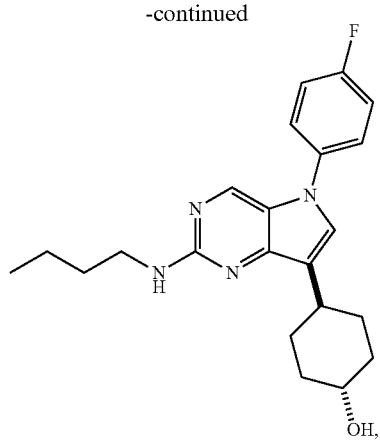

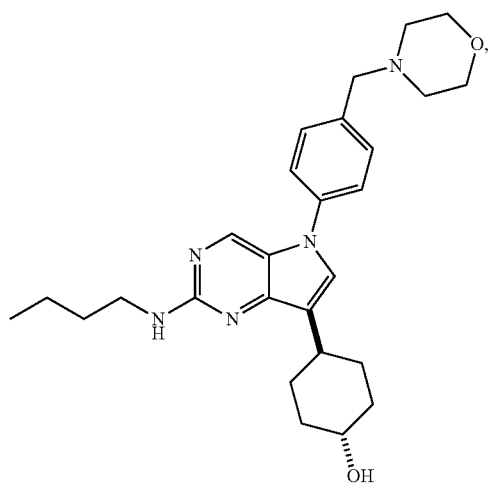

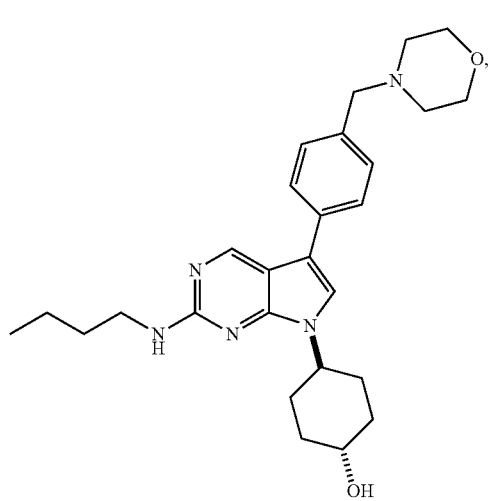

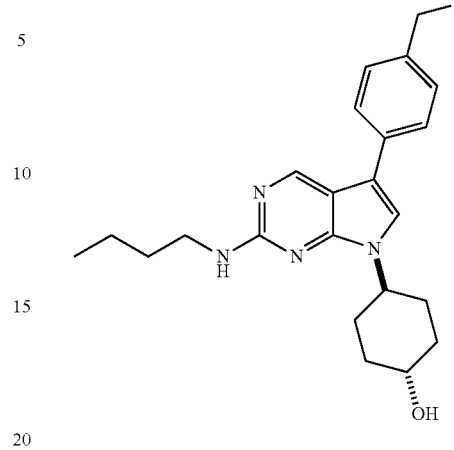

or a pharmaceutically acceptable salt thereof.

As in any embodiment above, a method wherein the compound of Formula I has the structure:

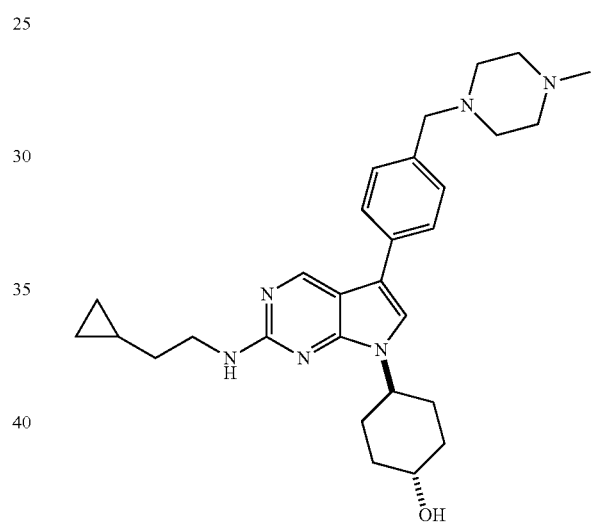

(UNC2371; MRX 2843) or a pharmaceutically acceptable salt thereof.

As in any embodiment above, a method wherein the EGFR inhibitor is selected from the group consisting of:

(a) the small organic molecule EGFR inhibitors gefitinib, erlotinib, lapatinib, Brigatinib (AP26113), Neratinib (HKI-272), AZD3759, AZ5104, CL-387785 (EKI-785), Canertinib (CI-1033), Poziotinib (HM781-36B), Osimertinib (AZD-9291), PD168393, CNX-2006, Rociletinib (CO-1686, AVL-301), WZ4002, Pelitinib (EKB-569), AC480 (BMS-599626), TAK-285, CUDC-101, AEE788 (NVP-AEE788), CP-724714, Dacomitinib (PF299804, PF299), AG-490 (Tyrphostin B42), AST-1306, OSI-420, WHI-P154, WZ3146, WZ8040, AZD8931 (Sapitinib), PD153035 HCl, Icotinib, Varlitinib, AZD-9291, AEE788 (NVP-AEE 788), AG-1478 (NSC 693255), AG-490, Anlotinib, ARRY-380, BIBX 1382, and BMS-690514; and (b) the monoclonal antibody EGFR inhibitors cetuximab, panitumumab, zalutumumab, nimotuzumab, and matuzumab.

As in any embodiment above, a method wherein the EGFR inhibitor has the structure of Formula XI:

(XI)

wherein:
n' is 0, 1, or 2;
m' is 0, 1, or 2, wherein m' and n' are not simultaneously 0;
W is —O— or —NH—;
$R^{11}$ is —$OR^{10}$;
each $R^{10}$ is independently $C_{1-4}$ alkyl or $C_{1-4}$ fluoroalkyl;
$R^{12}$ is —$CF_3$, Cl, or Br;
G is —O—, —$NR^{13}$—, —$S(O_2)$—, or —$CH(OR^{14})$—;
$R^{13}$ is —C(O)—$R^{10}$, —C(O)$OR^{10}$, —C(O)$NHR^{10}$, —$SO_2$—R, —$SO_2NH_2$, —C(O)—$C_{1-4}$ alkylene-OH or —$SO_2$—$C_{1-4}$ alkylene-OH;
$R^{14}$ is hydrogen, $C_{1-4}$ alkyl, or $C_{1-4}$ fluoroalkyl; and
$R^{15}$ is hydrogen or —C(O)$OR^{10}$;
or a pharmaceutically acceptable salt thereof.

As in any embodiment above, a method wherein G is —$NR^{13}$—.

As in any embodiment above, a method wherein W is —NH—.

As in any embodiment above, a method wherein $R^{12}$ is —$CF_3$.

As in any embodiment above, a method wherein n' is 1 and m' is 1.

As in any embodiment above, a method wherein the compound of Formula XI has the structure:

CO-1686 or a pharmaceutically acceptable salt thereof.

As in any embodiment above, a method wherein the EGFR inhibitor has the structure of Formula XII:

(XII)

wherein:
G is selected from 4,5,6,7-tetrahydropyrazolo[1,5-a]pyridin-3-yl, 1H-indol-3-yl, 1-methyl-1H-indol-3-yl and pyrazolo[1,5-a]pyridin-3-yl;
$R^{21}$ is selected from hydrogen, fluoro, chloro, methyl and cyano;
$R^{22}$ is selected from methoxy and methyl; and
$R^{23}$ is selected from (3R)-3-(dimethylamino)pyrrolidin-1-yl, (3S)-3-(dimethylamino)pyrrolidin-1-yl, 3-(dimethylamino)azetidin-1-yl, [2-(dimethylamino)ethyl]-(methyl)amino, [2-(methylamino)ethyl](methyl)amino, 5-methyl-2,5-diazaspiro[3,4]oct-2-yl, (3 aR,6aR)-5-methylhexa-hydropyrrolo[3,4-b]pyrrol-1 (2H)-yl, 1-methyl-1,2,3,6-tetrahydropyridin-4-yl, 4-methylpiperizin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-aminopropanoyl]piperazin-1-yl;
or a pharmaceutically acceptable salt thereof.

As in any embodiment above, a method wherein the EGFR inhibitor has the structure:

AZD9291 or a pharmaceutically acceptable salt thereof.

In an embodiment, a pharmaceutical composition comprising:
(a) a first active compound (e.g., a MER tyrosine kinase (MERTK) inhibitor); and
(b) an Epidermal Growth Factor Receptor (EGFR) inhibitor, in
(c) a pharmaceutically acceptable carrier (e.g., with the MERTK inhibitor and the EGFR inhibitor included in the carrier an amount effective to treat tumors in a subject in need thereof; and with the MERTK inhibitor included in the carrier an amount effective to enhance the efficacy of the EGFR inhibitor in treating the tumors.)

As in any embodiment above, a pharmaceutical composition in oral dosage form (e.g., a tablet or capsule).

As in any embodiment above, a pharmaceutical composition wherein the first active compound and the EGFR inhibitor are included in the composition in an amount having therapeutic synergy.

As in any embodiment above, a pharmaceutical composition wherein the first active compound comprises a compound of Formula I:

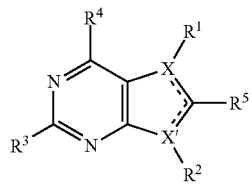

(I)

wherein:
one of X and X' is N and the other of X and X' is C;
one of the dashed lines in Formula I is a single bond and the other of the dashed lines in Formula I is a double bond;
$R^1$ is aryl, wherein the aryl is unsubstituted or substituted from 1 to 3 times with one or a combination of halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocycle-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano, where m=0, 1, 2 or 3, and wherein the alkyl or heterocycloalkyl-S(O)$_m$ can be substituted from 1 to 3 times with one or a combination of halo, alkyl, haloalkyl, or unsubstituted or substituted heterocycloalkyl, wherein the substituted heterocycloalkyl can be substituted from 1 to 3 times with one or a combination of halo, alkyl, or haloalky; or
$R^1$ is heteroaryl, wherein the heteroaryl is unsubstituted or substituted from 1 to 3 times with one or a combination of halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano, where m=0, 1, 2 or 3, and wherein the alkyl or heterocycloalkyl-S(O)$_m$ can be substituted from 1 to 3 times with one or a combination of halo, alkyl, haloalkyl, or unsubstituted or substituted heterocycloalkyl, wherein the substituted heterocycloalkyl can be substituted from 1 to 3 times with one or a combination of halo, alkyl, or haloalkyl;

$R^2$ is —$R^{5'}R^6$, where $R^{5'}$ is a covalent bond or C1 to C3 alkyl and $R^6$ is cycloalkyl, and wherein $R^6$ is optionally substituted from one to two times with independently selected polar groups;

$R^3$ is —$NR^7R^8$, where $R^7$ and $R^8$ are each independently selected from H, alkyl, arylalkyl, cycloalkylalkyl, heterocycloalkylalkyl, heteroarylalkyl, and alkoxyalkyl, each of which is optionally substituted one, two or three times with independently selected polar groups;

$R^4$ is H, lower alkyl, halo, or lower alkoxy; and
$R^5$ is H, lower alkyl, halo, or lower alkoxy;
or a pharmaceutically acceptable salt thereof.

As in any embodiment above, a pharmaceutical composition wherein the compound of Formula I has the structure of Formula IA:

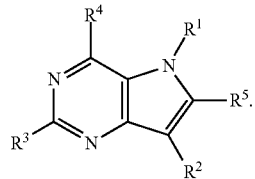

(IA)

As in any embodiment above, a pharmaceutical composition wherein the compound of Formula I has the structure of Formula IB:

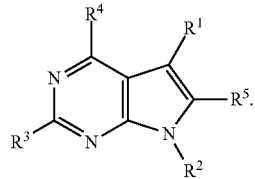

(IB)

As in any embodiment above, a pharmaceutical composition wherein $R^{5'}$ of the compound of Formula I is a covalent bond or C1 to C3 alkyl.

As in any embodiment above, a pharmaceutical composition wherein $R^1$ of the compound of Formula I is phenyl, or pyridyl, which phenyl or pyridyl is unsubstituted or substituted from 1 to 3 times with halo, amino, nitro, alkyl, alkoxyl, haloalkyl, cycloalkyl, heterocycloalkyl, aryl, or heteroaryl.

As in any embodiment above, a pharmaceutical composition wherein $R^8$ of the compound of Formula I is C1-C8 alkyl, or C1-C8 arylalkyl.

As in any embodiment above, a pharmaceutical composition wherein $R^6$ of the compound of Formula I is cyclohexyl.

As in any embodiment above, a pharmaceutical composition wherein $R^7$ of the compound of Formula I is H and/or $R^4$ of the compound of Formula I is H.

As in any embodiment above, a pharmaceutical composition wherein the compound of Formula I has the structure:

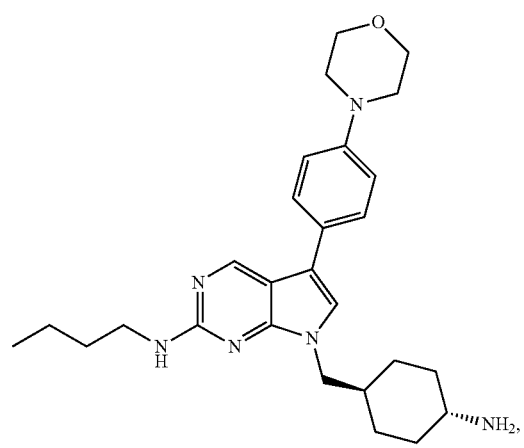
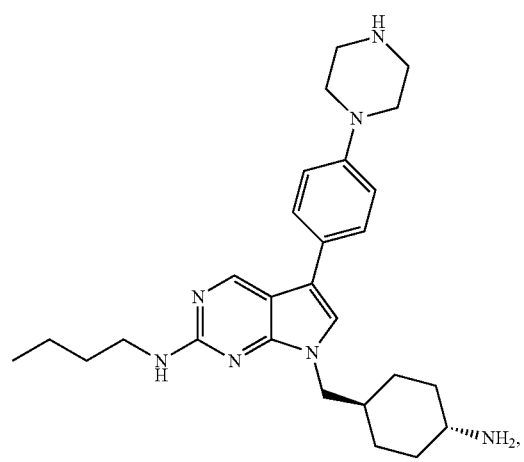
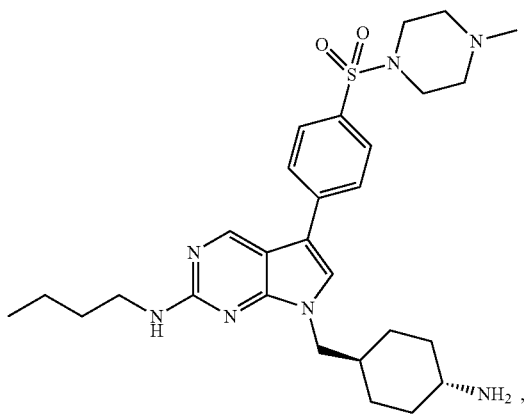
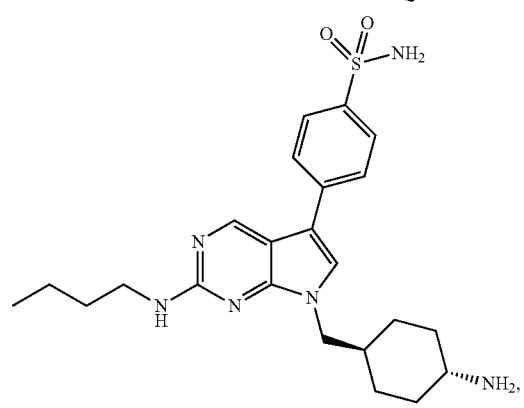
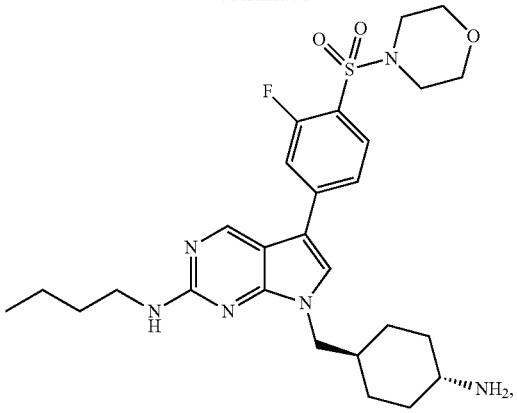
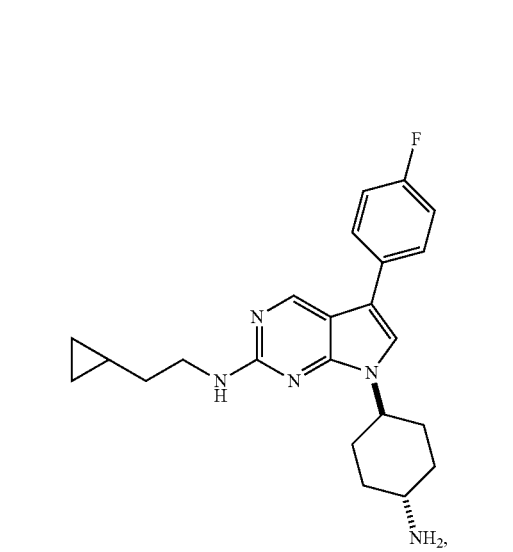
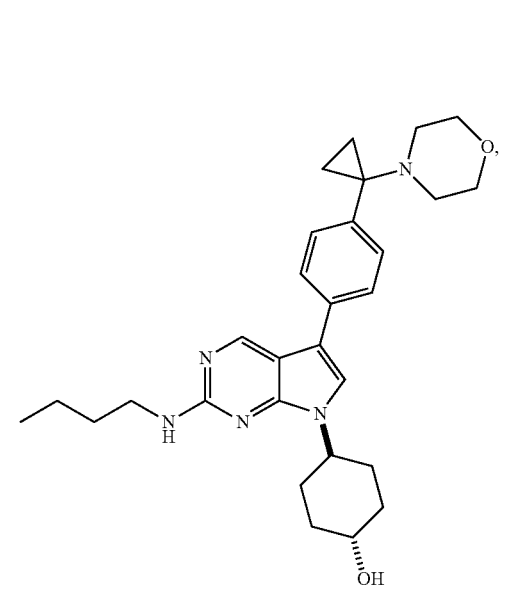

33
-continued
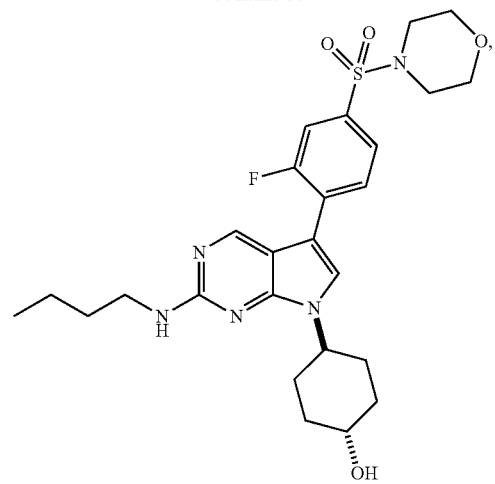
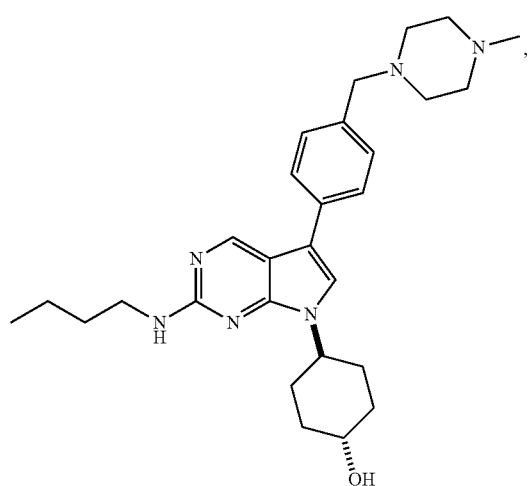
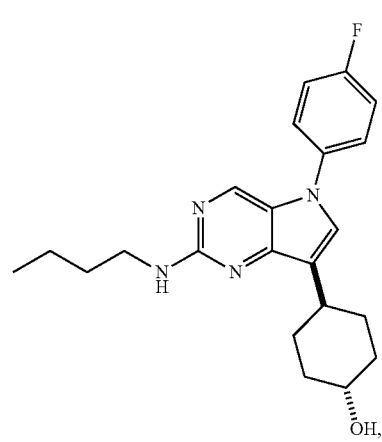
34
-continued
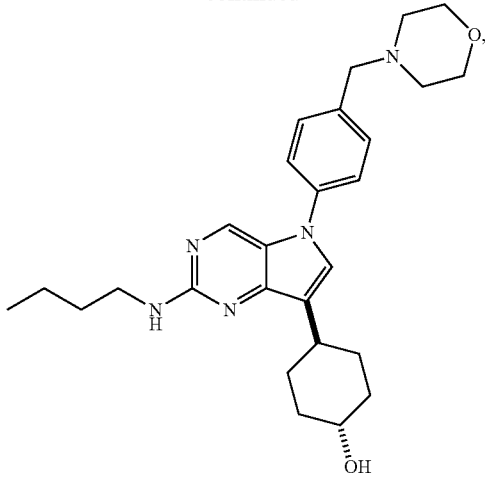
or a pharmaceutically acceptable salt thereof.
As in any embodiment above, a pharmaceutical composition wherein the compound of Formula I has the structure:

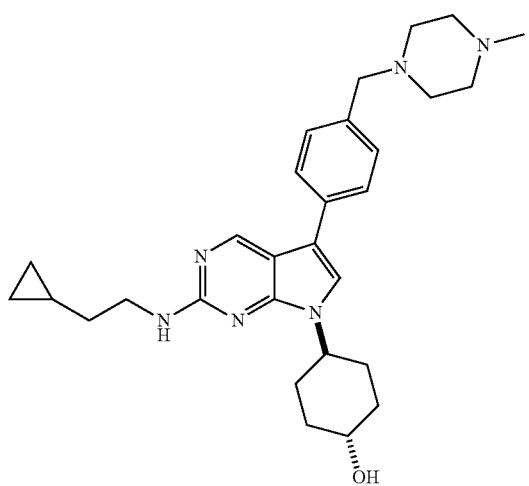

(UNC2371; MRX 2843) or a pharmaceutically acceptable salt thereof.

As in any embodiment above, a pharmaceutical composition wherein the EGFR inhibitor is selected from the group consisting of:

(a) the small organic molecule EGFR inhibitors gefitinib, erlotinib, lapatinib, Brigatinib (AP26113), Afatinib (BIBW2992), Neratinib (HKI-272), AZD3759, AZ5104, CL-387785 (EKI-785), Canertinib (CI-1033), Poziotinib (HM781-36B), Osimertinib (AZD-9291), PD168393, CNX-2006, Rociletinib (CO-1686, AVL-301), WZ4002, Pelitinib (EKB-569), AC480 (BMS-599626), TAK-285, CUDC-101, AEE788 (NVP-AEE788), CP-724714, Dacomitinib (PF299804, PF299), AG-490 (Tyrphostin B42), AST-1306, OSI-420, WHI-P154, WZ3146, WZ8040, AZD8931 (Sapitinib), PD153035 HCl, Icotinib, Varlitinib, AZD-9291, AEE788 (NVP-AEE 788), AG-1478 (NSC 693255), AG-490, Anlotinib, ARRY-380, BIBX 1382, and BMS-690514; and (b) the monoclonal antibody EGFR inhibitors cetuximab, panitumumab, zalutumumab, nimotuzumab, and matuzumab.

As in any embodiment above, a pharmaceutical composition wherein the EGFR inhibitor has the structure of Formula XI:

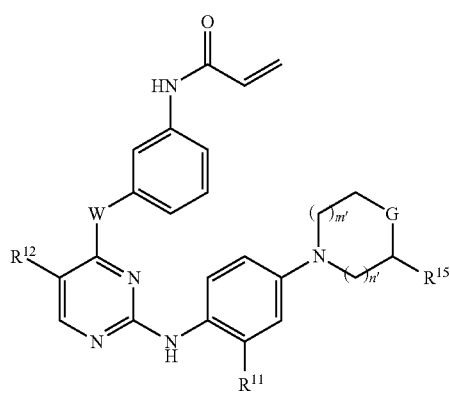

(XI)

wherein:
n' is 0, 1, or 2;
m' is 0, 1, or 2, wherein m' and n' are not simultaneously 0;

W is —O— or —NH—;
$R^{11}$ is —$OR^{10}$;
each $R^{10}$ is independently $C_{1-4}$ alkyl or $C_{1-4}$ fluoroalkyl;
$R^{12}$ is —$CF_3$, Cl, or Br;
G is —O—, —$NR^{13}$—, —$S(O_2)$—, or —$CH(OR^{14})$—;
$R^{13}$ is —C(O)—$R^{10}$, —C(O)$OR^{10}$, —C(O)$NHR^{10}$, —$SO_2$—R, —$SO_2NH_2$, —C(O)—$C_{1-4}$ alkylene-OH or —$SO_2$—$C_{1-4}$ alkylene-OH;
$R^{14}$ is hydrogen, $C_{1-4}$ alkyl, or $C_{1-4}$ fluoroalkyl; and
$R^{15}$ is hydrogen or —C(O)$OR^{10}$;

or a pharmaceutically acceptable salt thereof.

As in any embodiment above, a pharmaceutical composition wherein G is —$NR^{13}$—.

As in any embodiment above, a pharmaceutical composition wherein W is —NH—.

As in any embodiment above, a pharmaceutical composition wherein $R^{12}$ is —$CF_3$.

As in any embodiment above, a pharmaceutical composition wherein n' is 1 and m' is 1.

As in any embodiment above, a pharmaceutical composition wherein the compound of Formula XI has the structure:

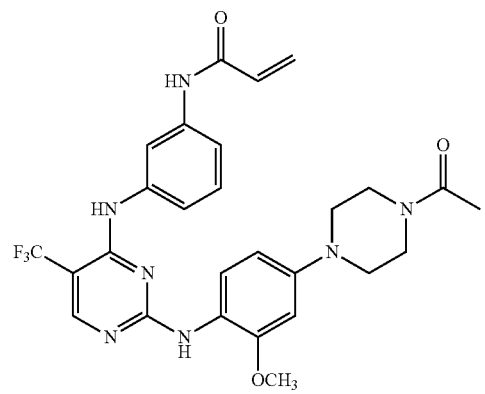

CO-1686 or a pharmaceutically acceptable salt thereof.

As in any embodiment above, a pharmaceutical composition wherein the EGFR inhibitor has the structure of Formula XII:

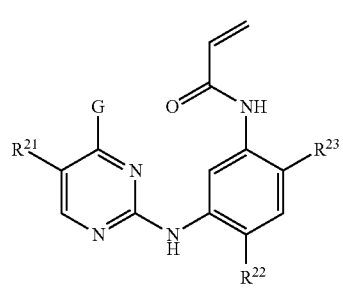

(XII)

wherein:
G is selected from 4,5,6,7-tetrahydropyrazolo[1,5-a]pyridin-3-yl, 1H-indol-3-yl, 1-methyl-1H-indol-3-yl and pyrazolo[1,5-a]pyridin-3-yl;

$R^{21}$ is selected from hydrogen, fluoro, chloro, methyl and cyano; $R^{22}$ is selected from methoxy and methyl; and $R^{23}$ is selected from (3R)-3-(dimethylamino)pyrrolidin-1-yl, (3S)-3-(dimethylamino)pyrrolidin-1-yl, 3-(dimethylamino)azetidin-1-yl, [2-(dimethylamino)ethyl]-(methyl)amino, [2-(methylamino)ethyl](methyl)amino, 5-methyl-2,5-diazaspiro[3,4]oct-2-yl, (3 aR,6aR)-5-methylhexa-hydropyrrolo[3,4-b]pyrrol-1(2H)-yl, 1-methyl-1,2,3,6-tetrahydropyridin-4-yl, 4-methylpiperizin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-aminopropanoyl]piperazin-1-yl;

or a pharmaceutically acceptable salt thereof.

As in any embodiment above, a pharmaceutical composition wherein the EGFR inhibitor has the structure:

AZD9291

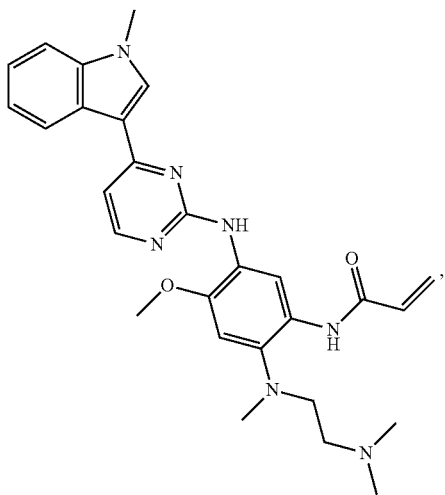

or a pharmaceutically acceptable salt thereof.

Still further embodiments are described below.

In an embodiment, a method of treating tumors in a mammalian subject in need thereof, comprising:
concurrently administering to the subject a MERTK tyrosine kinase inhibitor and an Epidermal Growth Factor Receptor (EGFR) inhibitor,
wherein the MERTK tyrosine kinase inhibitor is administered to the subject in an amount effective to enhance the efficacy of the EGFR inhibitor in treating the tumors.

As in any embodiment above, a method wherein the tumors comprise non-small cell lung cancer, glioblastoma, breast, head or neck, colon, gastric, pancreatic, or bladder cancer tumors.

As in any embodiment above, a method wherein the tumors comprise non-small cell lung cancer tumors.

As in any embodiment above, a method wherein the tumors comprise malignant primary tumors.

As in any embodiment above, a method wherein the tumors comprise metastatic secondary tumors.

As in any embodiment above, a method wherein the tumors comprise metastatic non-small cell lung cancer tumors in the brain.

As in any embodiment above, a method wherein:
cells of the tumors over-express wild-type EGFR, and/or cells of the tumors express a mutant EGFR.

As in any embodiment above, a method wherein said mutant EGFR is selected from the group consisting of the L858R activating mutant, the Exon 19 deletion activating mutant, the ΔE746-A750 activating mutant, the G719C activating mutant, the G719S activating mutant, the G719A activating mutant, the T790M resistance mutant, the C797S resistance mutant, and the D761Y resistance mutant. In an additional embodiment, the mutant EGFR is selected from the group consisting of the V689M, N700D, E709K/Q, S720P, ΔE746-T751, ΔE746-A750 (insRP), ΔE746-T751 (ins A/I), ΔE746-T751(ins VA), ΔE746-S752 (ins A/V), ΔE746-E749 (A750P), ΔE747-A750(ins P), ΔE747-T751, ΔE747-T751 (ins P/S), ΔE747-S752, ΔE747-752 (E746V), ΔE747-752 (P735S), ΔE747-S752 (ins Q), ΔE747-P753, ΔE747-P753 (ins S), ΔE752-I759, V765A, T783A, N826S, A839T, K846R, L861Q, and G863D mutants.

As in any embodiment above, a method wherein the first active compound and the EGFR inhibitor are administered in a synergistic effective amount.

As in any embodiment above, a method wherein the subject is human.

As in any embodiment above, a method wherein the method results in one or more of: (a) inhibition of tumor growth; (b) reduction in tumor size; (c) reduction in the number of tumors, and (d) decreased tumor burden in the subject.

As in any embodiment above, a method wherein the method prevents development of resistance to EGFR TKIs in EGFR mutant NSCLC cell lines.

As in any embodiment above, a method wherein the MERTK tyrosine kinase inhibitor is a compound of Formula I:

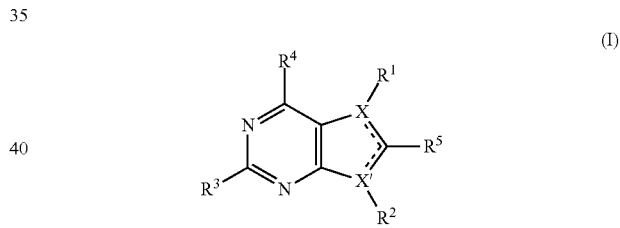

(I)

wherein:
one of X and X' is N and the other of X and X' is C;
one of the dashed lines in Formula I is a single bond and the other of the dashed lines in Formula I is a double bond;
$R^1$ is aryl, wherein the aryl is unsubstituted or substituted from 1 to 3 times with one or a combination of halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro, or cyano, where m=0, 1, 2 or 3, and wherein the alkyl or heterocycloalkyl-S(O)$_m$ can be substituted from 1 to 3 times with one or a combination of halo, alkyl, haloalkyl, or unsubstituted or substituted heterocycloalkyl, wherein the substituted heterocycloalkyl can be substituted from 1 to 3 times with one or a combination of halo, alkyl, or haloalky; or R¹ is heteroaryl, wherein the heteroaryl is unsubstituted or substituted from 1 to 3 times with one or a combination of halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano, where m=0, 1, 2 or 3, and wherein the alkyl or heterocycloalkyl-S(O)$_m$ can be substituted from 1 to 3 times with one or a combination of halo, alkyl, haloalkyl, or unsubstituted or substituted heterocycloalkyl, wherein the substituted heterocycloalkyl can be substituted from 1 to 3 times with one or a combination of halo, alkyl, or haloalkyl;

R² is —R⁵'R⁶, where R⁵' is a covalent bond or C1 to C3 alkyl and R⁶ is cycloalkyl, and wherein R⁶ is optionally substituted from one to two times with independently selected polar groups;

R³ is —NR⁷R⁸, where R⁷ and R⁸ are each independently selected from H, alkyl, arylalkyl, cycloalkylalkyl, heterocycloalkylalkyl, heteroarylalkyl, and alkoxyalkyl, each of which is optionally substituted one, two or three times with independently selected polar groups;

R⁴ is H, lower alkyl, halo, or lower alkoxy; and

R⁵ is H, lower alkyl, halo, or lower alkoxy;

or a pharmaceutically acceptable salt thereof.

As in any embodiment above, a method wherein a compound of Formula I has the structure of Formula IA:

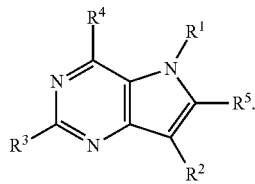

(IA)

As in any embodiment above, a method wherein the compound of Formula I has the structure of Formula IB:

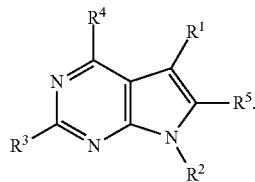

(IB)

As in any embodiment above, a method wherein R⁵' of the compound of Formula I is a covalent bond or C₁- to C₃ alkyl.

As in any embodiment above, a method wherein R¹ of the compound of Formula I is phenyl or pyridyl, wherein the phenyl or pyridyl is optionally substituted 1 to 3 times with halo, amino, nitro, alkyl, alkoxyl, haloalkyl, cycloalkyl, heterocycloalkyl, aryl, or heteroaryl.

As in any embodiment above, a method wherein R⁸ of the compound of Formula I is $C_{1-8}$ alkyl, or $C_{1-8}$ arylalkyl.

As in any embodiment above, a method wherein R⁶ of the compound of Formula I is cyclohexyl.

As in any embodiment above, a method wherein R⁷ of the compound of Formula I is H and/or R⁴ of the compound of Formula I is H.

As in any embodiment above, a method wherein the compound of Formula I has one of the following structures:

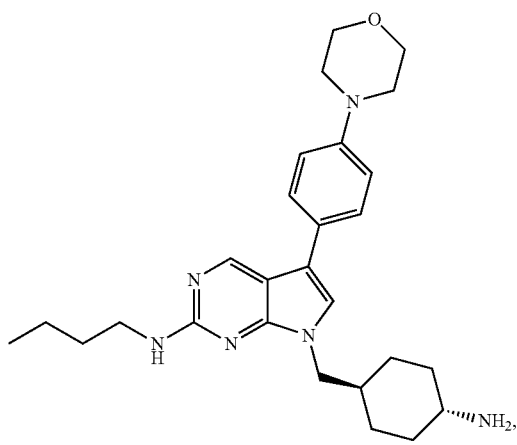

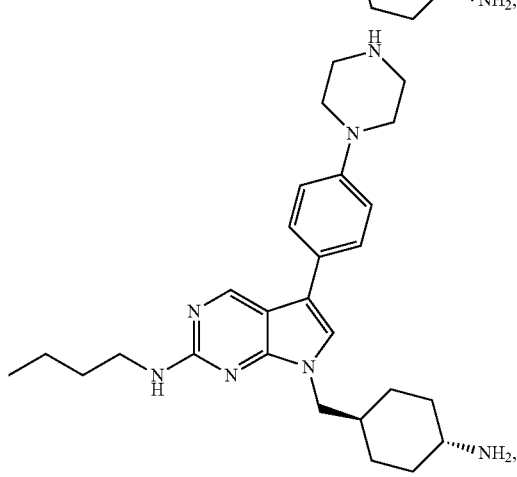

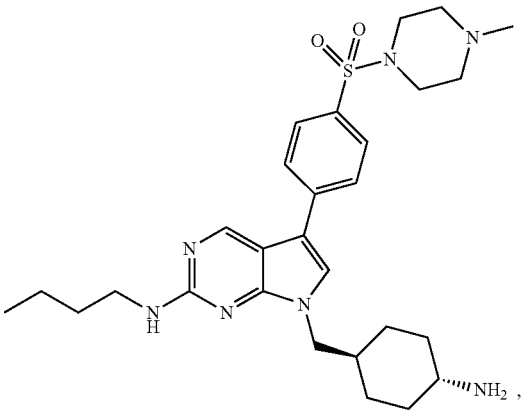

41
-continued
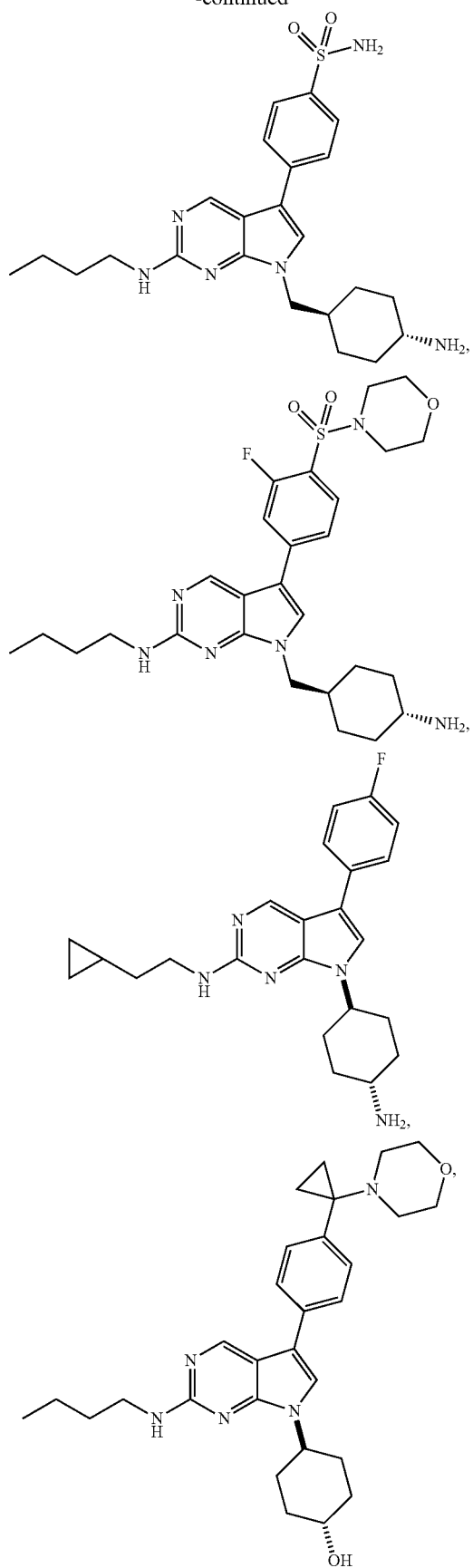
42
-continued
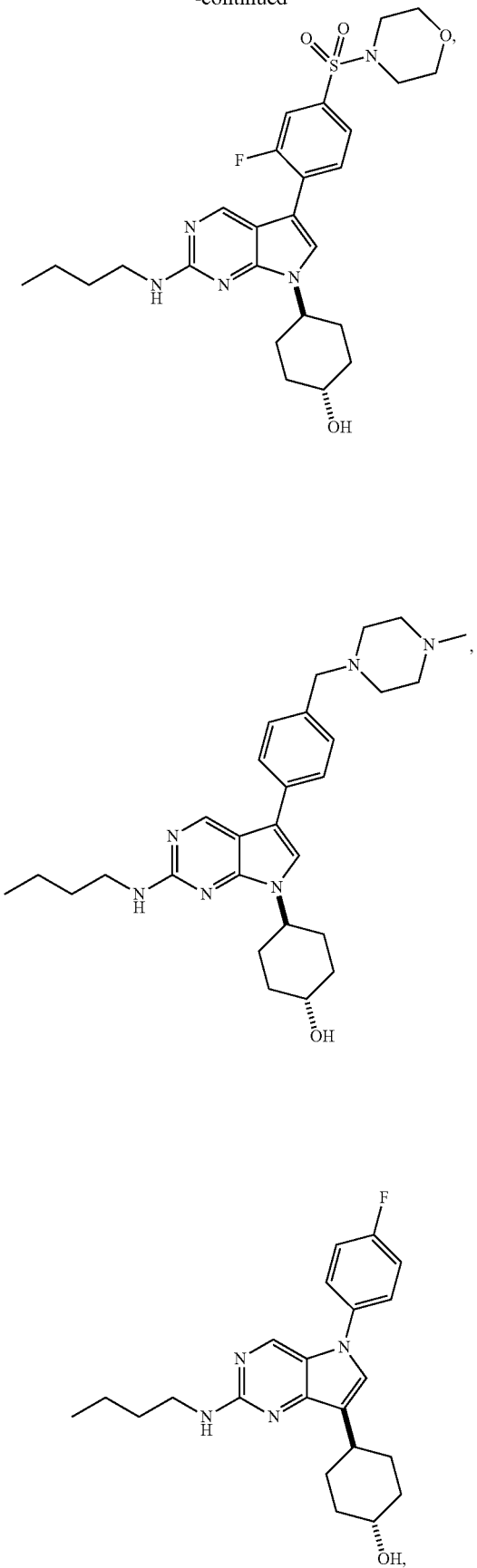

-continued

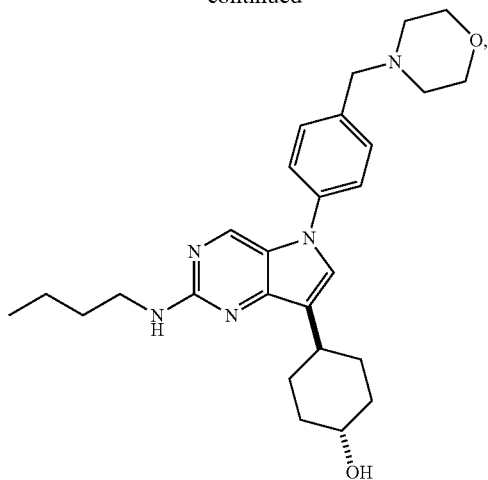

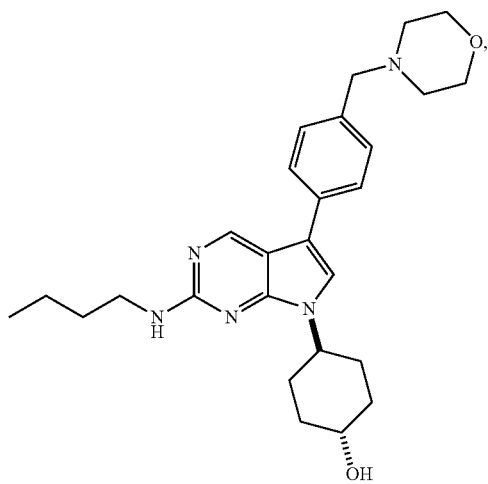

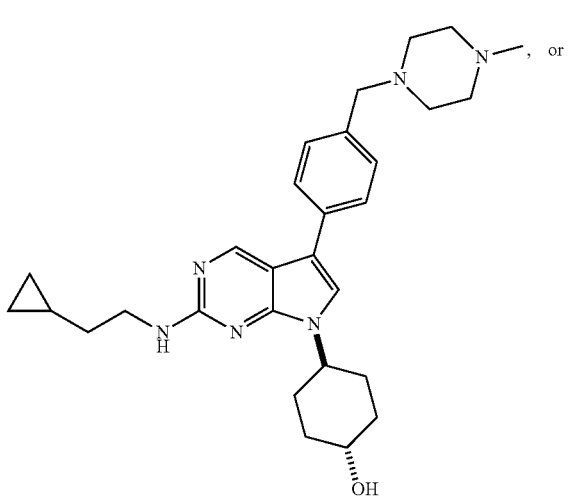

-continued

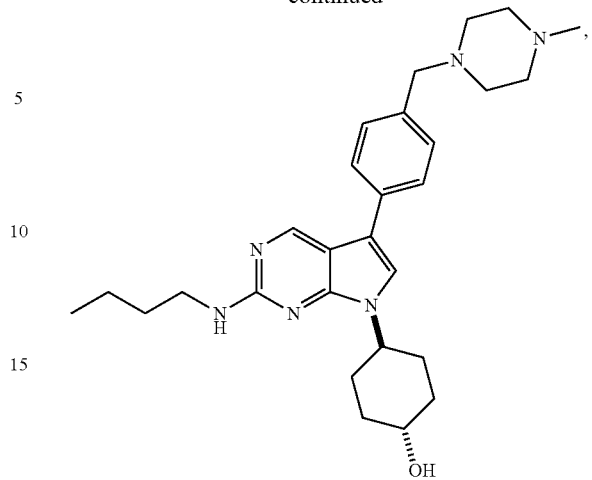

or a pharmaceutically acceptable salt thereof.

As in any embodiment above, a method wherein the compound of Formula I has the structure:

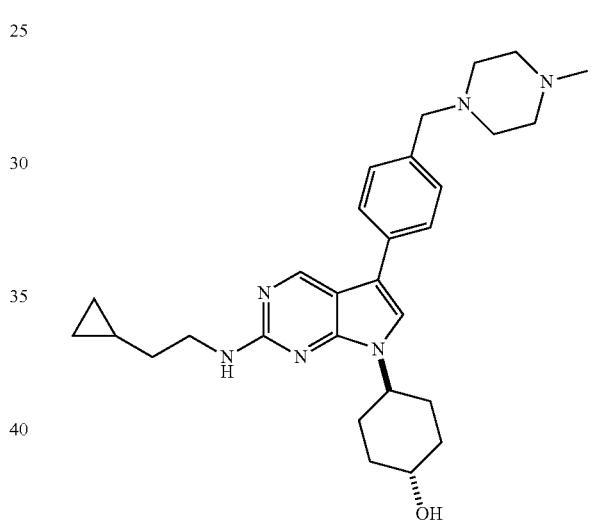

or a pharmaceutically acceptable salt thereof.

As in any embodiment above, a method wherein the EGFR inhibitor is selected from the group consisting of: gefitinib, erlotinib, lapatinib, Brigatinib (AP26113), Afatinib (BIBW2992), Neratinib (HKI-272), AZD3759, AZ5104, CL-387785 (EKI-785), Canertinib (CI-1033), Poziotinib (HM781-36B), Osimertinib (AZD-9291), PD168393, CNX-2006, Rociletinib (CO-1686, AVL-301), WZ4002, Pelitinib (EKB-569), AC480 (BMS-599626), TAK-285, CUDC-101, AEE788 (NVP-AEE788), CP-724714, Dacomitinib (PF299804, PF299), AG-490 (Tyrphostin B42), AST-1306, OSI-420, WHI-P154, WZ3146, WZ8040, AZD8931 (Sapitinib), PD153035 HCl, Icotinib, Varlitinib, AZD-9291, AEE788 (NVP-AEE 788), AG-1478 (NSC 693255), AG-490, Anlotinib, ARRY-380, BIBX 1382, BMS-690514, cetuximab, panitumumab, zalutumumab, nimotuzumab, and matuzumab.

As in any embodiment above, a method wherein the EGFR inhibitor is selected from the group consisting of Rociletinib (CO-1686), AZD-9291, and icotinib.

As in any embodiment above, a method wherein the EGFR inhibitor is CO-1686 and the MERTK TKI is MRX-2843.

As in any embodiment above, a method wherein the EGFR inhibitor is AZD-9291 and the MERTK TKI is MRX-2843.

As in any embodiment above, a method wherein the EGFR inhibitor is icotinib and the MERTK TKI is MRX-2843.

As in any embodiment above, a method wherein the EGFR inhibitor is icotinib and the MERTK TKI is MRX-2843.

In an embodiment, a pharmaceutical composition comprising a MERTK tyrosine kinase inhibitor, an Epidermal Growth Factor Receptor (EGFR) inhibitor, and a pharmaceutically acceptable carrier, wherein the MERTK tyrosine kinase inhibitor is present in an amount effective to enhance the efficacy of the EGFR inhibitor in treating the tumors.

As in any embodiment above, a pharmaceutical composition wherein the MERTK tyrosine kinase inhibitor is a compound of Formula I:

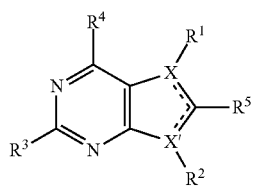

wherein:

one of X and X' is N and the other of X and X' is C;

one of the dashed lines in Formula I is a single bond and the other of the dashed lines in Formula I is a double bond;

$R^1$ is aryl, wherein the aryl is unsubstituted or substituted from 1 to 3 times with one or a combination of halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocycle-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano, where m=0, 1, 2 or 3, and wherein the alkyl or heterocycloalkyl-S(O)$_m$ can be substituted from 1 to 3 times with one or a combination of halo, alkyl, haloalkyl, or unsubstituted or substituted heterocycloalkyl, wherein the substituted heterocycloalkyl can be substituted from 1 to 3 times with one or a combination of halo, alkyl, or haloalky; or $R^1$ is heteroaryl, wherein the heteroaryl is unsubstituted or substituted from 1 to 3 times with one or a combination of halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano, where m=0, 1, 2 or 3, and wherein the alkyl or heterocycloalkyl-S(O)$_m$ can be substituted from 1 to 3 times with one or a combination of halo, alkyl, haloalkyl, or unsubstituted or substituted heterocycloalkyl, wherein the substituted heterocycloalkyl can be substituted from 1 to 3 times with one or a combination of halo, alkyl, or haloalkyl;

$R^2$ is —$R^{5'}R^6$, where $R^{5'}$ is a covalent bond or C1 to C3 alkyl and $R^6$ is cycloalkyl, and wherein $R^6$ is optionally substituted from one to two times with independently selected polar groups;

$R^3$ is —$NR^7R^8$, where $R^7$ and $R^8$ are each independently selected from H, alkyl, arylalkyl, cycloalkylalkyl, heterocycloalkylalkyl, heteroarylalkyl, and alkoxyalkyl, each of which is optionally substituted one, two or three times with independently selected polar groups;

$R^4$ is H, lower alkyl, halo, or lower alkoxy; and $R^5$ is H, lower alkyl, halo, or lower alkoxy;

or a pharmaceutically acceptable salt thereof.

As in any embodiment above, a pharmaceutical composition in oral dosage form.

In an embodiment, the pharmaceutical compositions described herein comprise a MERTK tyrosine kinase inhibitor, an EGFR inhibitor, and a pharmaceutically acceptable excipient, as described in any above embodiment.

EGFR expression is present in more than 60% of NSCLCs and only 17% of these tumors have EGFR mutations. Clinically available EGFR inhibitors have limited effect on wild-type EGFR expressing NSCLCs. Although EGFR inhibitors are effective for treatment of some NSCLCs expressing mutant EGFR, patients may have refractory disease and development of resistance to current EGFR-targeted therapies occurs (Noda, S., and Kanda, S., *Expert Rev. Respir. Med.*, 2016, 10(5):547-556), indicating a need for new therapies. Novel combination therapies that target MERTK, an oncogenic protein, and enhance sensitivity to EGFR inhibitors, thus reducing the incidence of therapeutic resistance in EGFR mutant NSCLCs, are needed.

As disclosed herein, cell-based screening identified CO1686, an EGFR tyrosine kinase inhibitor that synergistically inhibits expansion of the A549 NSCLC cell line when used in combination with MRX-2843, a novel MERTK-selective tyrosine kinase inhibitor.

As reported by Walter (Walter, A. O., et al., *Cancer Discov*, 2013. 3(12):1404-15), NSCLC cell lines with wild-type EGFR expression were resistant to CO-1686 treatment and NSCLC cell lines with EGFR mutation, including T790M (H1975), showed clear sensitivity to 1 μM CO1686.

As disclosed herein, a synergistic interaction between CO1686 and MRX-2843 was not observed in a normal human bronchial epithelial BEAS2B cell line that does not express MERTK or EGFR. Without being bound by theory, it is believed that the observed synergy in A549 cells was mediated by on-target inhibition. Synergistic growth inhibition mediated by CO1686 in combination with MRX-2843 was applicable to a panel of NSCLC cell lines with wild-type or mutant EGFR expression and co-expression of MERTK, irrespective of driver oncogene status.

A549 cells expressing MERTK shRNA exhibited increased sensitivity to CO1686 and siRNA-mediated EGFR inhibition compared to wild-type A549 cells and A549 cells expressing a non-targeting control shRNA, demonstrating that synergistic growth inhibition was both MERTK and EGFR dependent. Treatment with MRX-2843 sensitized NSCLC cell lines (with wild-type or mutant EGFR expression and co-expression of MERTK) to CO1686 in colony-forming assays. Also, combined treatment with MRX-2843 and CO1686 mediated greater inhibition of MERTK and EGFR phosphorylation compared to single agents in NSCLC cell lines. EGFR co-immunoprecipitated with both MERTK and AXL. Without being bound by theory, it is believed the co-immunoprecipitation indicates a physical interaction between these proteins.

Inhibition of MERTK sensitized wild-type and mutant EGFR expressing NSCLC cells to CO1686, a third generation EGFR inhibitor. This provides a novel therapeutic approach for treatment of a large fraction of patients with NSCLC who currently have limited options. Synergistic growth inhibition was specific for NSCLC cells and was not observed in normal human bronchial cells without MERTK and EGFR expression, providing a broad therapeutic window with limited toxicity to normal cells.

The foregoing is illustrative of the present invention, and is not to be construed as limiting thereof. The invention is defined by the following claims, with equivalents of the claims to be included therein.

That which is claimed:

1. A method of treating tumors, wherein said tumors comprise non-small cell lung cancer tumors in a mammalian subject in need thereof, comprising:

concurrently administering to said subject a MER tyrosine kinase inhibitor and an Epidermal Growth Factor Receptor (EGFR) inhibitor, wherein said MER tyrosine kinase inhibitor is

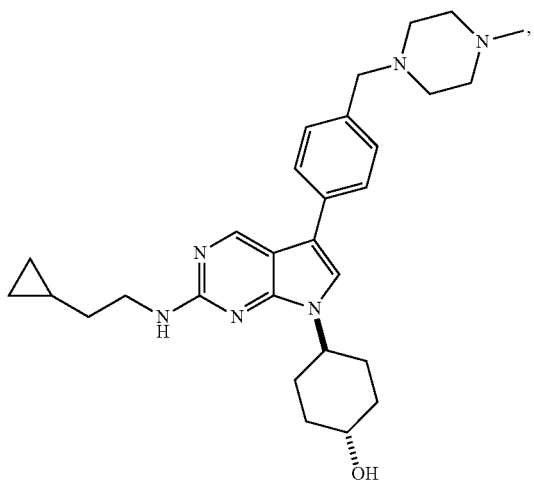

or a pharmaceutically acceptable salt thereof, and said EGFR inhibitor is Osimertinib (AZD-9291), and wherein said MER tyrosine kinase inhibitor is administered to said subject in an amount effective to enhance the efficacy of said EGFR inhibitor in treating said tumors.

2. The method of claim 1, wherein said tumors comprise malignant primary tumors.

3. The method of claim 1, wherein said tumors comprise metastatic secondary tumors.

4. The method of claim 1, wherein said tumors comprise metastatic non-small cell lung cancer tumors in the brain.

5. The method of claim 1, wherein:

cells of said tumors over-express wild-type EGFR, and/or cells of said tumors express a mutant EGFR.

6. The method of claim 5, wherein said mutant EGFR is selected from the group consisting of the L858R activating mutant, the Exon 19 deletion activating mutant, the ΔE746-A750 activating mutant, the G719C activating mutant, the G719S activating mutant, the G719A activating mutant, the T790M resistance mutant, the C797S resistance mutant, and the D761Y resistance mutant.

7. The method of claim 1, wherein said first active compound and said EGFR inhibitor are administered in a synergistic effective amount.

8. The method of claim 1, wherein said subject is human.

9. The method of claim 1, wherein said method results in one or more of: (a) inhibition of tumor growth; (b) reduction in tumor size; (c) reduction in the number of tumors, and (d) decreased tumor burden in the subject.

* * * * *